US008232296B2

(12) United States Patent
Briggner et al.

(10) Patent No.: US 8,232,296 B2
(45) Date of Patent: Jul. 31, 2012

(54) SALT 628

(75) Inventors: Lars-Erik Briggner, Lund (SE); Per Tomas Klingstedt, Lund (SE); Hans Roland Lönn, Lund (SE); Robert Zuban, Lund (SE); Marie-Lyne Alcaraz, Leicestershire (GB); Robert Anthony Nixon, Leicestershire (GB); Andrew James Watts, Leicestershire (GB)

(73) Assignee: Astrazeneca AB, Sodertalje (SE)

( * ) Notice: Subject to any disclaimer, the term of this patent is extended or adjusted under 35 U.S.C. 154(b) by 163 days.

(21) Appl. No.: 12/706,313

(22) Filed: Feb. 16, 2010

(65) Prior Publication Data
US 2010/0216843 A1    Aug. 26, 2010

Related U.S. Application Data

(60) Provisional application No. 61/154,099, filed on Feb. 20, 2009.

(51) Int. Cl.
*A61K 31/4439* (2006.01)
*C07D 401/14* (2006.01)

(52) U.S. Cl. ........................................ 514/333; 546/256

(58) Field of Classification Search .................. 546/256; 514/333
See application file for complete search history.

(56) References Cited

U.S. PATENT DOCUMENTS

| | | | |
|---|---|---|---|
| 4,181,658 A | 1/1980 | Hitzel et al. | |
| 4,186,200 A | 1/1980 | Kubo et al. | |
| 5,441,960 A | 8/1995 | Bernstein et al. | |
| 5,521,179 A | 5/1996 | Bernstein et al. | |
| 6,028,081 A | 2/2000 | Sada et al. | |
| 6,627,646 B2 * | 9/2003 | Bakale et al. | 514/322 |
| 6,977,266 B2 | 12/2005 | Tada et al. | |
| 6,979,690 B2 | 12/2005 | Gymer et al. | |
| 7,629,362 B2 | 12/2009 | Mitsuya et al. | |
| 2004/0023973 A1 | 2/2004 | Nagato et al. | |
| 2004/0082619 A1 | 4/2004 | Tada et al. | |
| 2004/0235761 A1 | 11/2004 | Furuta et al. | |
| 2005/0101590 A1 | 5/2005 | Yasui et al. | |
| 2005/0288290 A1 | 12/2005 | Borzilleri et al. | |
| 2006/0035938 A1 | 2/2006 | Bladh et al. | |
| 2006/0052411 A1 | 3/2006 | Tada et al. | |
| 2006/0100249 A1 | 5/2006 | Smith | |
| 2006/0211695 A1 | 9/2006 | Borzilleri et al. | |
| 2006/0270666 A1 | 11/2006 | Bladh et al. | |
| 2007/0010551 A1 | 1/2007 | Bladh et al. | |
| 2007/0043036 A1 | 2/2007 | Hansen et al. | |
| 2007/0203129 A1 | 8/2007 | Andersson et al. | |
| 2007/0213323 A1 | 9/2007 | Imogai et al. | |
| 2008/0103139 A1 | 5/2008 | Ishizuka et al. | |
| 2009/0105239 A1 | 4/2009 | Brimert et al. | |
| 2009/0131483 A1 | 5/2009 | Hansen et al. | |
| 2009/0131486 A1 | 5/2009 | Hansen et al. | |
| 2009/0209539 A1 | 8/2009 | Leblanc et al. | |
| 2009/0209555 A1 | 8/2009 | Hansen et al. | |
| 2010/0216843 A1 | 8/2010 | Briggner et al. | |
| 2010/0280048 A1 | 11/2010 | Ainge et al. | |
| 2011/0003858 A1 | 1/2011 | Bergstrom et al. | |

FOREIGN PATENT DOCUMENTS

| | | |
|---|---|---|
| EP | 0008864 A1 | 3/1980 |
| EP | 1300396 A1 | 4/2003 |
| EP | 1357111 A1 | 10/2003 |
| EP | 1465626 B1 | 10/2004 |
| EP | 1598349 A1 | 11/2005 |
| EP | 1806342 A1 | 7/2007 |
| GB | 2383326 A | 6/2003 |
| GB | 2392910 A | 3/2004 |
| JP | 2152966 A | 6/1990 |
| WO | WO-98/24780 A2 | 6/1998 |
| WO | WO-01/96308 A1 | 12/2001 |
| WO | WO-02/053543 A1 | 7/2002 |
| WO | WO-03/015798 | 2/2003 |
| WO | WO-03/047577 A2 | 6/2003 |
| WO | WO-03/070277 A1 | 8/2003 |
| WO | WO-2004/020410 A2 | 3/2004 |
| WO | WO-2004/043924 A1 | 5/2004 |
| WO | WO-2004/081001 A1 | 9/2004 |
| WO | WO-2005/021509 A1 | 3/2005 |
| WO | WO-2005/021512 A1 | 3/2005 |
| WO | WO-2005/026123 A1 | 3/2005 |
| WO | WO-2005/026124 A1 | 3/2005 |
| WO | WO-2005/080372 A1 | 9/2005 |
| WO | WO-2005/082864 A1 | 9/2005 |
| WO | WO-2006/004636 A2 | 1/2006 |
| WO | WO-2006/030032 A1 | 3/2006 |
| WO | WO-2006/046778 A1 | 5/2006 |
| WO | WO-2006/082412 A2 | 8/2006 |
| WO | WO-2006/098683 A1 | 9/2006 |
| WO | WO-2006/098684 A1 | 9/2006 |
| WO | WO-2006/116713 A1 | 11/2006 |
| WO | WO-2006/136857 A1 | 12/2006 |
| WO | WO-2007/107706 A2 | 9/2007 |

(Continued)

OTHER PUBLICATIONS

CMU Pharmaceutical polymorphism, internet p. 1-3 (2002) printout Apr. 3, 2008.*
Singhal et al., "Drug Polymorphism, etc.," Advanced Drug Delivery reviews 56, p. 335-347 (2004).*
Concise Encyclopedia Chemistry, NY: Walter de Gruyter, 1993, 872-873.*
Jain et al., "Polymorphism in Pharmacy", Indian Drugs, 1986, 23(6) 315-329.*
Muzaffar et al., "Polymorphism and Drug Availability, etc.," J of Pharm. (Lahore), 1979, 1(1), 59-66.*
U.S. Pharmacopia #23, National Formulary #18, 1995, 1843-1844.*
Doelker, english translation of S.T.P, Pratiques (1999), 9(5), 399-409, pp. 1033.*

(Continued)

*Primary Examiner* — Patricia Morris
(74) *Attorney, Agent, or Firm* — Astrazeneca AB

(57) ABSTRACT

6-Methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide 4-methylbenzenesulfonate and a novel crystalline form thereof are disclosed together with processes for preparing such salt and form, pharmaceutical compositions comprising such a salt and form, and the methods of treatment using such a salt and form.

3 Claims, 8 Drawing Sheets

FOREIGN PATENT DOCUMENTS

| WO | WO-2007/129060 A1 | 11/2007 |
|---|---|---|
| WO | WO-2007/129962 A1 | 11/2007 |
| WO | WO-2007/129963 A1 | 11/2007 |
| WO | WO-2008/006583 A1 | 1/2008 |
| WO | WO-2008/030158 A1 | 3/2008 |
| WO | 2008/104752 A1 | 9/2008 |
| WO | WO-2008/104752 A1 | 9/2008 |
| WO | 2009/058076 A1 | 5/2009 |
| WO | WO-2009/058076 A1 | 5/2009 |
| WO | WO-2009/061271 A1 | 5/2009 |
| WO | 2010/094964 A1 | 8/2010 |

OTHER PUBLICATIONS

Doelker, english translation of Ann. Pharm. Fr., 2002, 60: 161-176, pp. 1-39.*

Taday et al., "Using Terahertz, etc.," J of Pharm. Sci., 92(4), 2003, 831-838.*

Otuska et al., "Effect of Polymorphic, etc.," Chem. Pharm. Bull., 47(6) 852-856 (1999).*

Restriction Requirement mailed on Oct. 29, 2009 for U.S. Appl. No. 10/572,706, AstraZeneca Reference No. 101226.

Non-Final Office Action mailed on Feb. 17, 2010 for U.S. Appl. No. 10/572,706, AstraZeneca Reference No. 101226.

Ex-Parte Quayle Action mailed Jul. 21, 2010 for U.S. Appl. No. 10/572,706, AstraZeneca Reference No. 101226.

Notice of Allowance mailed Nov. 5, 2010 for U.S. Appl. No. 10/572,706, AstraZeneca Reference No. 101226.

Interview Summary mailed Nov. 5, 2010 for U.S. Appl. No. 10/572,706, AstraZeneca Reference No. 101226.

Notice of Allowance mailed Jul. 15, 2011 for U.S. Appl. No. 10/572,706, AstraZeneca Reference No. 101226.

Eistert, et al., "Synthese und Reaktionen substituierter Pyrrolin-2,3-dione mit Diazoalkanen," *Justus Liebigs Ann. Chem.* (1976), pp. 1023-1030.

Bauer, et al., "1.5-Benzodiazepin-trione und ihre Vorstufen", *Justis Liebings Ann. Chem.*, vol. 762, pp. 73-82 (1972).

Chughtai, et al., "Potential Role of Inhibitors of Neutrophil Elastase in Treating Diseases of the Airway", *Journal of Aerosol Medicine*, vol. 17 (6), pp. 289-298 (2004).

Friedman, "Future Treatment Strategies for COPD", *clinical CORNERSTONE—COPD*, vol. 5 (1), pp. 45-51 (2004).

Ohbayashi, "Current Synthetic Inhibitors of Human Neutrophil Elastase in 2005", *Expert Opin. Ther. Patents*, vol. 15 (7), pp. 759-771 (2005).

Ohbayashi, "Novel Neutrophil Elastase Inhibitors as a Treatment for Neutrophil-Predominant Inflammatory Lung Diseases", *The Investigational Drugs Journal*, vol. 5 (9), pp. 910-923 (2002).

Ohbayashi, "Neutrophil Elastase inhibitors as Treatment for COPD", *Expert Opinion on Investigational Drugs*, vol. 11 (7), pp. 965-980 (2002).

Okayama, et al., "Clinical Effects of a Neutrophil Elastase Inhibitor, Sivelestat, in Patients with Acute Respiratory Distress Syndrome", *Journal of Anesthesia*, vol. 20, pp. 6-10, (2006).

Sato, et al., "Nuetrophil Elastase and Cancer", *Surgical Oncology*, vol. 15, pp. 217-222 (2006).

Shimizu, et al., "A Mechanism of Antigen-Induced Mucus Production in Nasal Epithelium of Sensitized Rats", *Am. J. Respir. Crit. Care Med.*, vol. 161 (5), pp. 1648-1654 (2000).

Uktainets, et al., "4-Hydroxy-2-Quinolones, 23. N-(2-Thiazolyl)Amides of 1-R-2-Oxo-4-Hydroxyquinoline-3-Carboxylic Acids—a new Group of Potential Antiflammatory Agents", *Chemistry of Heterocyclic Compounds*, vol. 30 (10), pp. 1211-1213 (1994).

Wright, et al., "A Neutrophil Elastase Inhibitor Reduces Cigarette Smoke-Induced Remodelling of Lung Vessels", *Eur. Respir. J.*, vol. 22, pp. 77-81 (2003).

Zeiher, et al., "Neutrophil Elastase and Acute Lung Injury: Prosepects for Sivelestat and Other Neutrophil Elastase Inhibitors as Therapeutics", *Crit. Care Med.*, vol. 30 (5), pp. S281-S287 (2002).

Harayama, et al., "Hydrolysis Products of Flavins (Isoalloxazines)", *J. Chem. Soc. Perkin Trans. I*, pp. 75-83 (1987).

Beilstein Institute for Organic Chemistry, XP002481053 & KHIM Geterotsikl Soedin, vol. 34 (1), pp. 73-76 (1998).

STN International, File CAPLUS, CAPLUS accession No. 1995:456529, Document No. 123:198678, Ukrainets, I.V. et al.: "4-Hydroxy-2-Quinolones. 23. N-(2-Thiazolyl)Amides of 1-Substituted 4-Hydroxy-2-Oxoquinoline-3-Carboxylic Acids—a New Group of Potential anti-Flammatory Drugs"; & Khimiya geterotsiklicheskikh Soedinenii (10), 1397-9 (1994).

STN International, Vile CAPLUS, CAPLUS accession No. 1990:611864, Document No. 113:211864, Otsuka Pharmaceutical Co., Ltd.: "4-Hydroxycarbostyrils as Anti-Inflammatory and Antiallergy Agents",& JP, A2, 02152966, 19900612 (1990).

U.S. Appl. No. 12/895,995, filed Oct. 1, 2010.

* cited by examiner

X-ray powder diffraction diagram of compound (I) tosylate Form A

Differential scanning calorimetry (DSC) trace and a thermal gravimetric analytical (TGA) trace of compound (I) tosylate Form A Comparative dissolution profiles for compound (I) tosylate Form A tablets (corresponding to 30 mg strength of compound (I)) containing either microcrystalline cellulose or isomalt in pH 6.8 dissolution medium.

Blood concentration (nM) in a dog after administration of compound (I) tosylate in capsule and compound (I) free base administered as an aqueous suspension.

Dissolution profile of a film-coated tablet composition containing compound (I) tosylate Form A according to Example 10 (square data points) and crystalline compound (I) tosylate Form A in a capsule (diamond data points)

Dissolution profile of tablet compositions containing 5% and 0% dibasic calcium phosphate described in Table 7 of Example 13.

X-ray powder diffraction diagram of compound (I) tosylate Form B

X-ray powder diffraction diagram of compound (I) 2,5-dimethylbenzenesulfonate

SALT 628

CROSS REFERENCE TO RELATED APPLICATIONS

The present application claims benefit under 35 U.S.C. §119(e) of U.S. Provisional Application Ser. No. 61/154,099 filed on Feb. 20, 2009.

FIELD OF THE INVENTION

The present invention discloses a novel salt of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide, a novel crystalline form of such salt, processes for preparing such salt and form, pharmaceutical compositions comprising such a salt and form, and the use of such a salt and form in therapy.

BACKGROUND OF THE INVENTION

WO 2005/026123, which is incorporated herein by reference in its entirety, teaches a class of neutrophil elastase inhibitors that are useful in therapy.

WO 2005/026123 further discloses a specific neutrophil elastase inhibitor compound identified therein as 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide (Example 94, page 85). This compound is designated herein as compound (I).

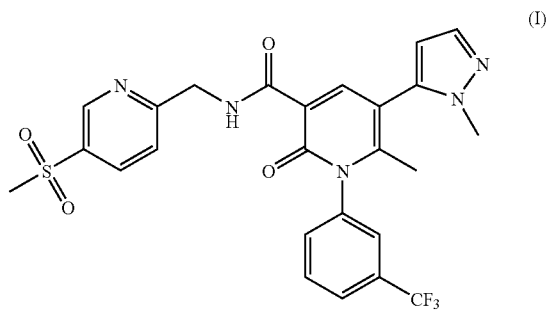
(I)

WO 2005/026123 further discloses a process for the preparation of compound (I).

Thus, in one embodiment of WO 2005/026123, compound (I) is prepared by the route shown in Scheme 1:

Scheme 1

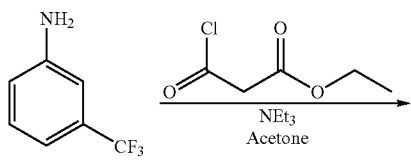

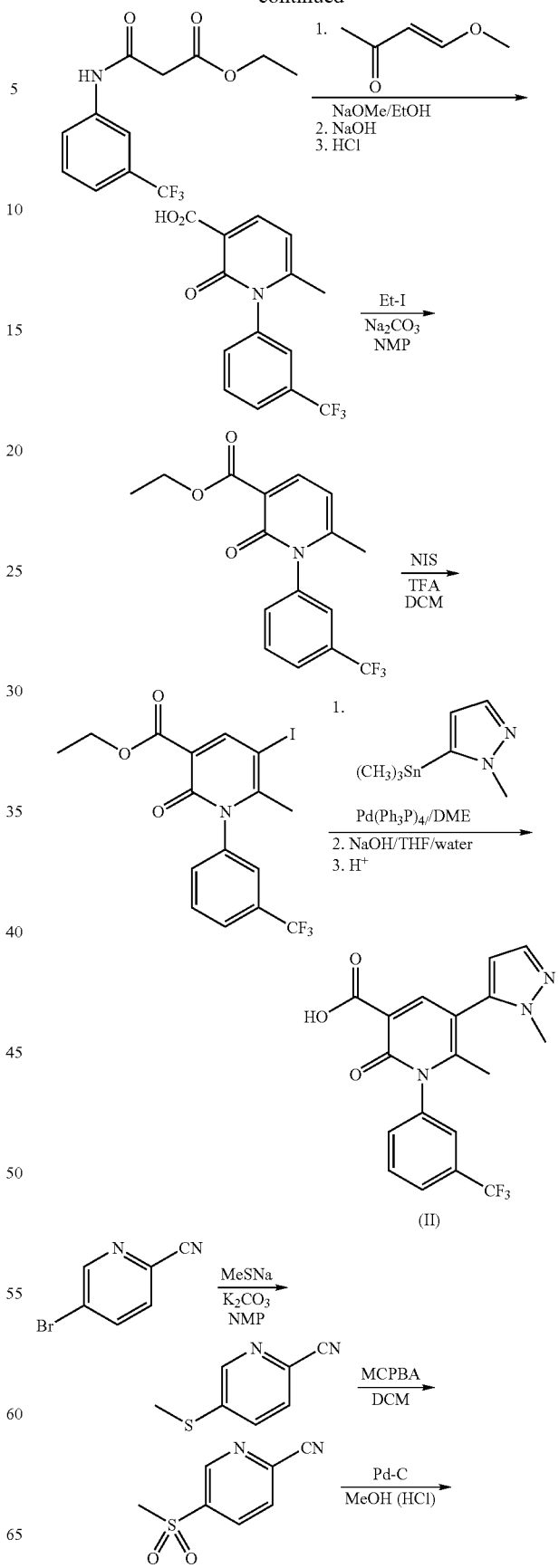

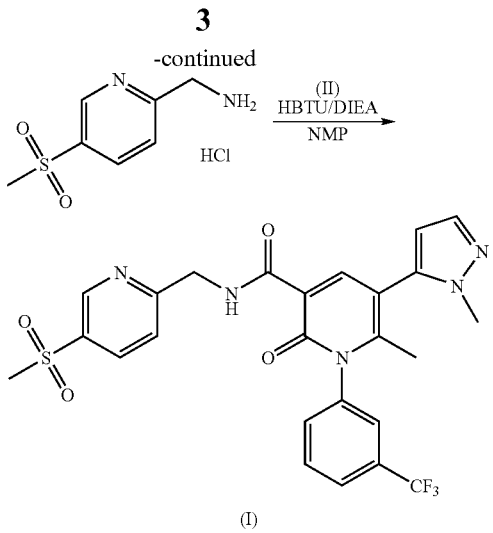

The obtained compound (I) was purified by preparative HPLC and freeze-dried to give the free base as a white solid. No specific salts nor any crystalline forms of compound (I) are disclosed in WO 2005/026123.

Compound (I) is a potent neutrophil elastase inhibitor and as such is useful in therapy.

However, compound (I) as the free base is poorly soluble and predictions indicated that the compound (administered as the free base) would demonstrate solubility limited absorption at high doses (for example doses greater than approximately 10 to 20 mg).

In order to prepare pharmaceutical formulations containing compound (I) as the active ingredient for administration to humans there is a need to produce compound (I) in a stable and more soluble form, such as a stable crystalline form, having consistent solid state physical properties which allow pharmaceutical processing.

There is thus a need to find way(s) to enable the poorly soluble pharmacologically active compound (I) to be absorbed to a sufficient degree within such a time frame following oral administration that the concentration of the active compound (I) in the biological fluid(s) is sufficient to get a desired pharmacological effect over a period of time.

The present invention provides a novel salt of compound (I) and a stable crystalline form of such a salt that has consistent and advantageous physical properties. Furthermore, as an additional independent feature the present invention also provides a formulation making it possible for the pharmacologically active compound (I) to be absorbed to the desired degree.

DISCLOSURE OF THE INVENTION

Figure 1:
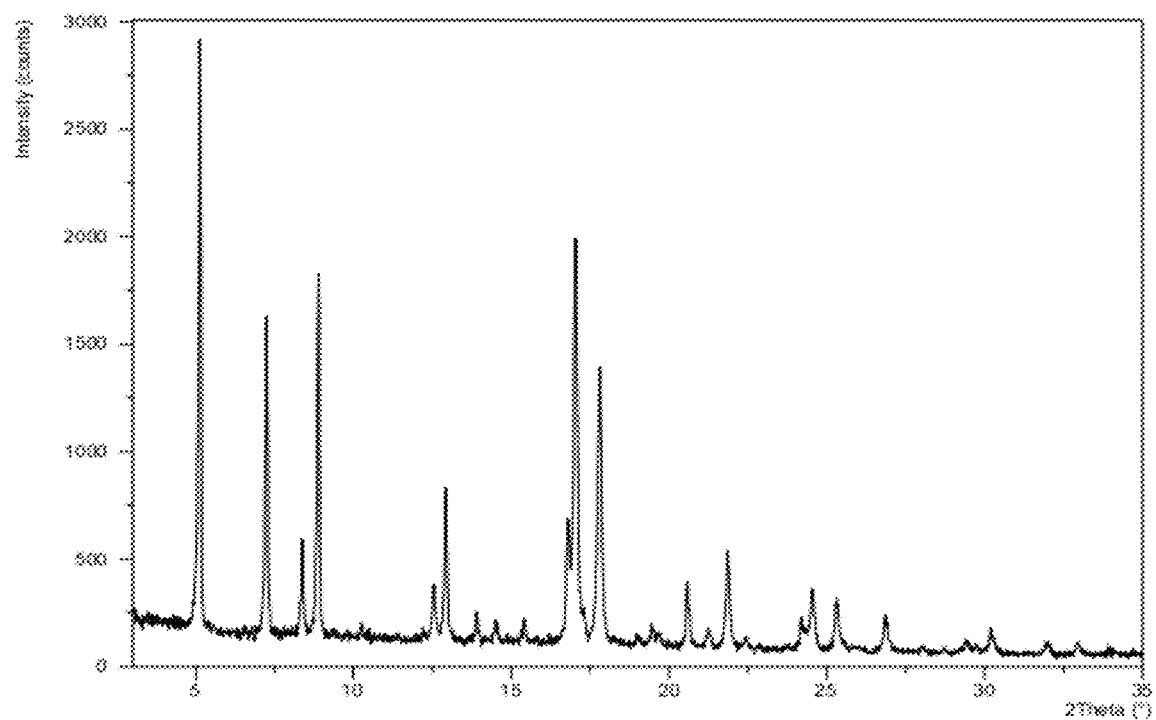
FIG. 1 is an X-ray powder diffraction (XRPD) diagram of compound (I) tosylate Form A. The x-axis shows the 2-theta value and the y-axis the intensity.

It has now surprisingly been found that the tosylate (4-methylbenzenesulfonate) salt of 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide, (hereafter compound (I) tosylate), possesses vastly improved solid state physical properties compared to those of the parent compound (I) free base.

A thorough salt screening experiment was carried out on compound (I). This found that compound (I) tosylate has solid state properties suitable to allow processing into tablets. Furthermore, compound (I) tosylate also has further advantageous properties including a high transient solubility and a rapid intrinsic dissolution rate.

Several salts of compound (I) with strong organic and inorganic acids have been prepared and tested as described below.

TABLE 1

| Salt of compound (I) | Solid Form | Solubility (mg/ml) |
|---|---|---|
| Tosylate | Crystalline | 1.2 |
| p-Xylene-2-sulfonate | Crystalline | 1.3 |
| Chloride | Amorphous | 0.047 |
| Mesylate | Crystalline | 0.43 |
| Esylate | Crystalline | 0.096 |
| 1,5-Naphthalenedisulfonate | Amorphous | not tested |
| Sulfate | Amorphous | not tested |
| Compound (I) free base | Crystalline | 0.040 |

"p-Xylene-2-sulfonate" in Table 1 is the 2,5-dimethylbenzenesulfonate salt of compound (I).

The solubility (mg/ml) shown in Table 1 was measured after 1 hour in 900 ml of 0.1 M HCl and at 75 rpm and 37° C. using a Zymark Multidose G3 system. Analysis was made by UV spectrophotometer with a detection wavelength of 337 nm.

The high transient solubility and fast dissolution of compound (I) tosylate suggest that an improved bioavailability could be expected at doses where the free base of compound (I) would suffer from solubility-limited absorption. An increased bioavailability was demonstrated in the dog for compound (I) tosylate, where the bioavailability of the compound (I) tosylate Form A, administered in a capsule was approximately 3 times higher than that seen for the corresponding compound (I) free base formulated as a crystalline suspension (see Bioavailability Example and FIG. 4).

Therefore compound (I) tosylate is expected to improve the aqueous solubility of compound (I) for a sufficient period of time to allow enhanced absorption in man. Without wishing to be limited by theory, the enhanced solubility of compound (I) tosylate may arise from a combination of the inherent higher solubility of the compound (I) tosylate, and a continued high solubility when the compound (I) precipitates from solution as amorphous material, in aqueous media. The observed improved solubility may therefore reflect both the solubility of the amorphous material and the solubility of the compound (I) tosylate, which will be present in-vivo in varying ratios following oral administration of compound (I) tosylate as a result of the kinetic balance between dissolution and precipitation of compound (I). Table 2 shows the solubility of compound (I) tosylate in various dissolution media with time. In Table 2, the columns marked "modification" refer to the form of the solid present in the dissolution medium at the relevant time point indicated. The data in Table 2 indicate that the solubility remains high for at least 3 hours, particularly at low pH, representative of the pH found in the stomach. The time period of 3 hours represents a time span relevant for absorption from the GI tract in humans, though over a longer period of time the material eventually crystallises out after dissociation as the crystalline parent free base compound (I) and this explains the much lower solubility observed after 24 hours.

zenesulfonate can be obtained as a stable anhydrous crystalline solid having excellent solid state properties.

According to a first aspect of the invention there is provided 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide 4-methylbenzenesulfonate (compound (I) tosylate).

Suitably the compound (I) tosylate is crystalline.

In one embodiment, the invention provides a crystalline form, which is 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide 4-methylbenzenesulfonate designated "compound (I) tosylate Form A".

Compound (I) tosylate Form A provides an X-ray powder diffraction pattern substantially as shown in FIG. 1. The most prominent peaks of compound (I) tosylate Form A measured using $CuK_\alpha$ radiation are shown in Table 3.

TABLE 3

| Angle 2-Theta° (2θ) |
|---|
| 5.1 |
| 7.3 |
| 8.4 |
| 8.9 |
| 12.6 |
| 12.9 |
| 16.8 |
| 17.0 |
| 17.8 |
| 20.6 |
| 21.9 |

In one embodiment there is provided compound (I) tosylate Form A, wherein said Form A has an X-ray powder diffraction pattern measured using $CuK_\alpha$ radiation with at least one specific peak at 2θ=about 5.1, 7.3, 8.9, 17.0 or 17.8°.

In another embodiment there is provided compound (I) tosylate Form A, wherein said Form A has an X-ray powder

TABLE 2

| Solvent | Solubility 1 h (μM) | Modification | Solubility 3 h (μM) | Modification | Solubility 24 h (μM) | Modification |
|---|---|---|---|---|---|---|
| 0.1 M HCl pH 1.0 | 1531 ± 129 | Some salt, mostly amorphous (I) | 1098 ± 145 | Traces of salt, mostly amorphous (I) | 58.4 ± 1.2 | Amorphous (I) and parent crystalline (I) |
| 0.2 M Phosphate buffer pH 3.0 | 493 ± 97 | Amorphous (I) | 492 ± 115 | Small traces of parent crystalline (I) | 11.8 ± 0.9 | Parent crystalline (I) |
| 0.2 M Phosphate buffer pH 5.0 | 490 ± 42 | Amorphous (I) | 460 ± 54 | Amorphous (I) | 12.2 ± 0.6 | Parent crystalline (I) |
| 0.2 M Phosphate buffer pH 6.5 | 416 ± 48 | Amorphous (I) | 363 ± 86 | Amorphous (I) | 10.1 ± 0.8 | Parent crystalline (I) |
| 0.2 M Phosphate buffer pH 8 | 412 ± 29 | Amorphous (I) | 240 ± 35 | Amorphous (I) | 8.4 ± 0.7 | Parent crystalline (I) |

Other aspects of the invention are directed to pharmaceutical compositions containing compound (I) tosylate and to uses of the salt. These aspects of the invention are described in more detail hereafter.

6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide 4-methylbenzenesulfonate diffraction pattern measured using $CuK_\alpha$ radiation with specific peaks at 2θ=about 5.1, 7.3, 8.9, 17.0 and 17.8°.

In another embodiment there is provided compound (I) tosylate Form A, wherein said Form A has an X-ray powder diffraction pattern measured using $CuK_\alpha$ radiation with at least one specific peak at 2θ=about 5.1, 7.3, 8.9, 12.9, 16.8, 17.0, 17.8 or 21.9°.

In another embodiment there is provided compound (I) tosylate Form A, wherein said Form A has an X-ray powder diffraction pattern measured using CuK$_\alpha$ radiation with specific peaks at 2θ=about 5.1, 7.3, 8.9, 12.9, 16.8, 17.0, 17.8 and 21.9°.

In another embodiment, the invention provides compound (I) tosylate Form A, characterised by having an X-ray powder diffraction pattern measured using CuK$_\alpha$ radiation substantially the same as that shown in FIG. 1.

Figure 2:
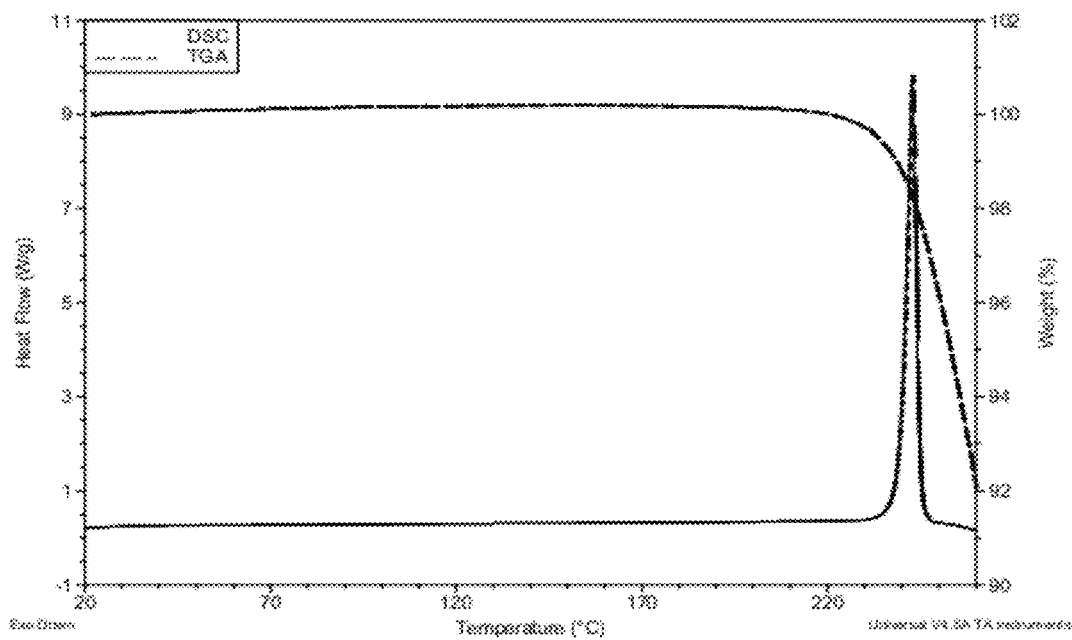
FIG. 2 is a differential scanning calorimetry (DSC) trace (solid line) and a thermal gravimetric analytical (TGA) trace (dashed line) of compound (I) tosylate Form A. The x-axis shows temperature (° C.) and the y-axis heat flow (watts/g) (DSC) and sample weight % (TGA).

In another embodiment, the invention provides compound (I) tosylate Form A characterised by having a differential scanning calorimetric (DSC) trace substantially the same as that shown in FIG. 2.

The crystalline Forms of compound (I) tosylate according to the invention are preferably substantially pure, meaning that the crystalline Form of the compound of formula (I) includes less than 10%, preferably less than 5%, more preferably less than 3%, even more preferably less than 1% by weight of impurities, including other crystalline Forms of the compound.

Thus, in one embodiment, the invention provides a substantially pure compound (I) tosylate Form A, characterised by having an X-ray powder diffraction pattern measured using CuK$_\alpha$ radiation comprising specific peaks at 2θ=about 5.1, 7.3, 8.9, 17.0 and 17.8°.

In another embodiment, the invention provides a substantially pure compound (I) tosylate Form A, characterised by having an X-ray powder diffraction pattern measured using CuK$_a$ radiation comprising specific peaks at 2θ=about 5.1, 7.3, 8.9, 12.9, 16.8, 17.0, 17.8 and 21.9°.

In another embodiment, the invention provides a substantially pure compound (I) tosylate Form A characterised by having an X-ray powder diffraction pattern measured using CuK$_\alpha$ radiation substantially the same as that shown in FIG. 1.

Compound (I) tosylate Form A is obtained as an off-white crystalline powder comprising crystals normally exhibiting needle like morphology. The material is highly crystalline as determined by X-ray powder diffraction measurements.

The crystal structure of compound (I) tosylate Form A was determined by single crystal X-ray diffraction. In the crystal, the molecules are packed in a monoclinic space group (P2$_1$/n). There are 4 molecules in the asymmetric unit cell (a=5.10 Å, b=30.01 Å, c=21.05 Å). The close packing, resulting in a lack of internal space, is manifested in a relatively high density of 1.48 g/mL.

The simulated X-ray powder diffraction pattern of compound (I) tosylate Form A calculated using the single crystal X-ray diffraction data agrees well with the experimentally determined pattern shown in FIG. 1. The positions of the diffracted peaks have a very close match and the differences in relative peak intensities are attributable to preferred orientation effects.

When heated, Form A exhibits a melting/degradation onset at about 237° C. No significant weight loss was observed up to 200° C., but due to degradation a significant weight loss is initiated close to melting (FIG. 2). Thus, Form A is thermally stable at pharmaceutically relevant temperatures.

Humidity sorption measurements using gravimetrical vapour sorption (GVS) showed compound (I) tosylate Form A to have a very low humidity uptake of around 0.2% at 80% relative humidity (RH). As such, compound (I) tosylate Form A is right at the border between slightly hygroscopic and non hygroscopic, according to the criteria defined in the European Pharmacopoeia.

Compound (I) tosylate Form A has excellent and highly advantageous solid state properties. It is crystalline, non to slightly hygroscopic, and is thermally stable to 200° C., showing neither solvent loss nor any other thermal event prior to melting (see DSC and TGA traces, FIG. 2).

The solid state stability of compound (I) tosylate Form A was studied under four sets of conditions: at 25° C./desiccated; at 25° C./60% relative humidity (RH); 40° C./75% RH and 60° C./75% RH. Samples were examined (LC and XRPD) after 4, 8 and 12 weeks and chemical and physical stability were evaluated. Except for some potential chemical degradation under the stressed 60° C./75% RH condition, no significant chemical or physical changes were observed under any condition or at any timepoint tested. It was concluded that compound (I) tosylate Form A has excellent and advantageous chemical and physical stability in the solid state under pharmaceutically relevant storage conditions.

The stoichiometry of the Compound (I) tosylate Form A is 1:1 compound (I) to tosylate. The stoichiometry of the salt can be determined using known methods, for example $^1$H NMR.

Figure 7:
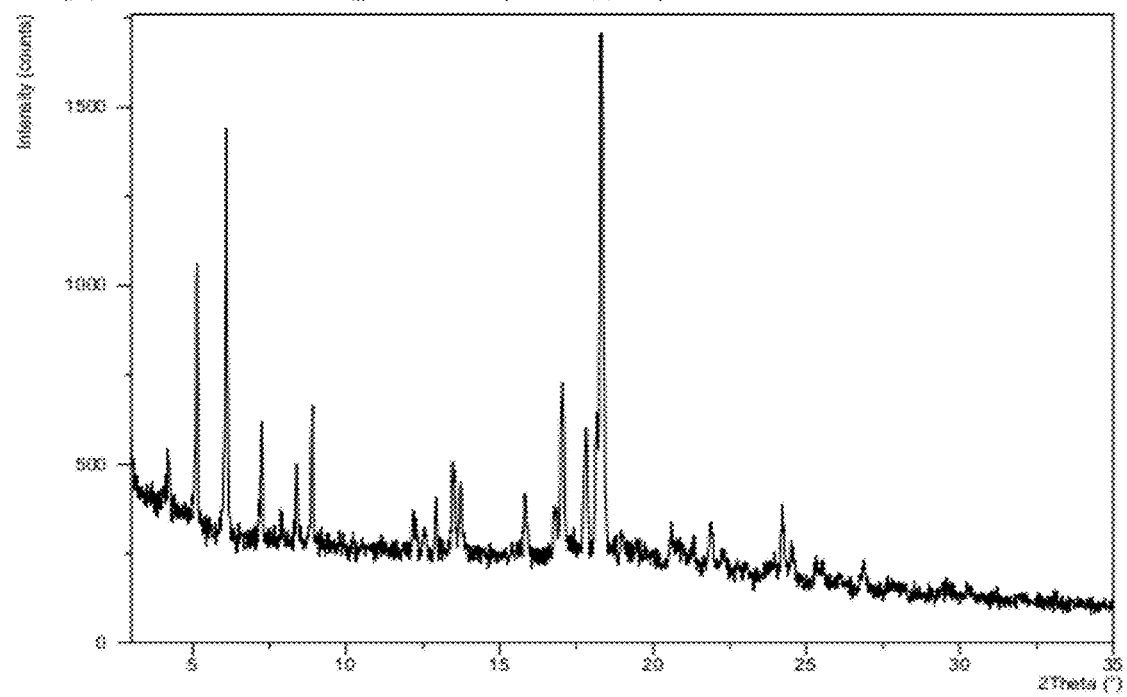
FIG. 7 is an X-ray powder diffraction diagram of compound (I) tosylate Form B. The x-axis shows the 2-theta value and the y-axis the intensity.

We have also found another crystalline form of compound (I) tosylate, hereafter compound (I) tosylate Form B. Compound (I) tosylate Form B provides an X-ray powder diffraction pattern substantially as shown in FIG. 7. Compound (I) tosylate Form B may be prepared as described in the Examples.

Compound (I) 2,5-dimethylbenzenesulfonate has also been found to be crystalline and has advantageous dissolution properties compared to compound (I) free base. Compound (I) 2,5-dimethylbenzenesulfonate is a salt formed between compound (I) and 2,5-dimethylbenzenesulfonic acid (p-xylene-2-sulfonic acid).

Accordingly as a further feature of the present invention there is provided 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide 2,5-dimethylbenzenesulfonate Form A (hereafter compound (I) 2,5-dimethylbenzenesulfonate Form A).

Figure 8:
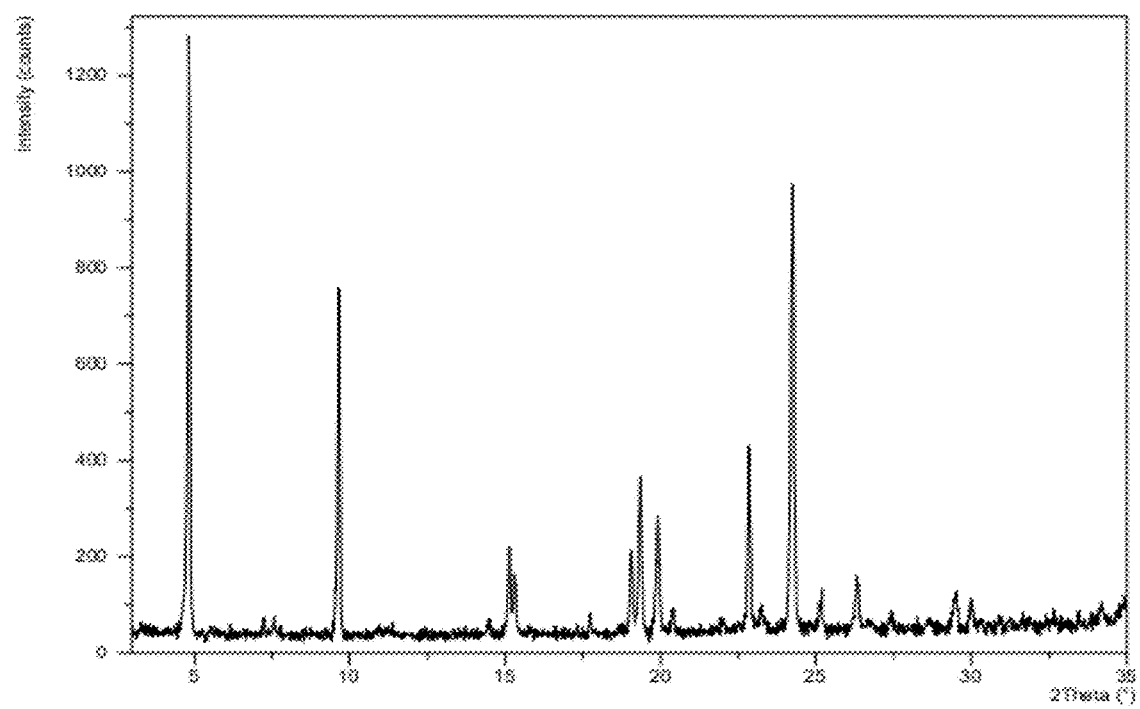
FIG. 8 shows an X-ray powder diffraction diagram of compound (I) 2,5-dimethylbenzenesulfonate Form A. The x-axis shows the 2-theta value and the y-axis the intensity.

Compound (I) 2,5-dimethylbenzenesulfonate Form A is crystalline and provides an X-ray powder diffraction pattern substantially as shown in FIG. 8.

In one embodiment there is provided compound (I) 2,5-dimethylbenzenesulfonate Form A, having an X-ray powder diffraction pattern measured using CuK$_\alpha$ radiation with at least one specific peak at 2θ=about 9.7, 22.8 or 24.2°.

In another embodiment there is provided compound (I) 2,5-dimethylbenzenesulfonate Form A, having an X-ray powder diffraction pattern measured using CuK$_\alpha$ radiation with at least one specific peak at 2θ=about 4.8, 9.7, 15.1, 15.3, 19.1, 19.4, 19.9, 22.8 or 24.2°.

In one embodiment there is provided compound (I) 2,5-dimethylbenzenesulfonate Form A, having an X-ray powder diffraction pattern measured using CuK$_\alpha$ radiation with specific peaks at 2θ=about 9.7, 22.8 and 24.2°.

In another embodiment there is provided compound (I) 2,5-dimethylbenzenesulfonate Form A, having an X-ray powder diffraction pattern measured using CuK$_\alpha$ radiation with specific peaks at 2θ=about 4.8, 9.7, 15.1, 15.3, 19.1, 19.4, 19.9, 22.8 and 24.2°.

In another embodiment there is provided compound (I) 2,5-dimethylbenzenesulfonate Form A, characterised by having an XPRD pattern measured using CuK$_\alpha$ radiation substantially the same as that shown in FIG. 8.

Compound (I) 2,5-dimethylbenzenesulfonate Form A may be prepared by crystallisation from a suitable solvent such as acetonitrile, using analogous methods to those described in the Examples herein.

Where reference is made to the salts of compound (I) being crystalline, such as the compound (I) tosylate Form A and compound (I) 2,5-dimethylbenzenesulfonate Form A, suitably the degree of crystallinity as determined by X-ray powder diffraction data is for example greater than about 60%, such as greater than about 80%, particularly greater than about 90%, more particularly greater than about 95%. In embodiments of the invention, the degree of crystallinity as determined by X-ray powder diffraction data is greater than about 98%, wherein the % crystallinity refers to the % by weight of the total sample mass which is crystalline.

In the preceding paragraphs defining the X-ray powder diffraction peaks for the crystalline forms of compound (I) tosylate Form A and compound (I) 2,5-dimethylbenzenesulfonate Form A, the term "about" is used in the expression "... at 2θ=about..." to indicate that the precise position of peaks (i.e. the recited 2-theta angle values) should not be construed as being absolute values because, as will be appreciated by those skilled in the art, the precise position of the peaks may vary slightly between one measurement apparatus and another, from one sample to another, or as a result of slight variations in measurement conditions utilised. It is also stated in the preceding paragraphs that the compound (I) tosylate Form A provides X-ray powder diffraction patterns 'substantially' the same as the X-ray powder diffraction patterns shown in FIG. 1, and has substantially the most prominent peaks (2-theta angle values) shown in Table 3. It is to be understood that the use of the term 'substantially' in this context is also intended to indicate that the 2-theta angle values of the X-ray powder diffraction patterns may vary slightly from one apparatus to another, from one sample to another, or as a result of slight variations in measurement conditions utilised, so the peak positions shown in the Figures or quoted in the Tables are again not to be construed as absolute values.

In this regard, it is known in the art that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions and sample preparation. For example, persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute (for further information see Jenkins, R & Snyder, R. L. 'Introduction to X-Ray Powder Diffractometry' John Wiley & Sons, 1996). Therefore, it shall be understood that the crystalline forms of compound (I) tosylate described herein are not limited to the crystals that provide X-ray powder diffraction patterns identical to the X-ray powder diffraction pattern shown in FIG. 1, and any crystals providing X-ray powder diffraction patterns substantially the same as those shown in FIG. 1 fall within the scope of the present invention. A person skilled in the art of X-ray powder diffraction is able to judge the substantial identity of X-ray powder diffraction patterns.

Generally, a measurement error of a diffraction angle in an X-ray powder diffractogram is about 2-theta=0.5° or less, and such degree of a measurement error should be taken into account when considering the X-ray powder diffraction patterns in FIG. 1 and when interpreting the peak positions referred to in the text above and in Table 3.

The melting points and DSC data described herein are described in more detail hereinafter. A person skilled in the art will appreciate that slight variations in the melting point measured by DSC may occur as a result of variations in sample purity, sample preparation and the measurement conditions (e.g. heating rate). It will be appreciated that alternative readings of melting point may be given by other types of equipment or by using conditions different to those described hereinafter. Hence the melting point and endotherm figures quoted herein are not to be taken as absolute values and such measurement errors are to be taken into account when interpreting DSC data. Typically, melting points may vary by ±5° C. or less.

The crystalline forms of compound (I) tosylate according to the invention may also be characterised and/or distinguished from other physical forms using other suitable analytical techniques, for example NIR spectroscopy or solid state nuclear magnetic resonance spectroscopy.

The chemical structure of compound (I) tosylate of the present invention can be confirmed by routine methods for example proton nuclear magnetic resonance (NMR) analysis.

In the context of the present invention, the salts of compound (I) described herein include a crystalline material in which compound (I) and the acid (for example the 4-methylbenzenesulfonic acid) are ionized or alternatively, where both components utilise prominent intermolecular interactions, such as hydrogen bonding, to combine and yield a uniform crystalline material (a co-crystal). It will be appreciated that a salt according to the invention may be partially ionic and partially co-crystal.

Preparation of Compound (I) Tosylate Form A

Compound (I) tosylate Form A is reproducibly produced when 6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide 4-methylbenzenesulfonate is crystallised from acetonitrile. Compound (I) tosylate Form A can also be crystallised from tetrahydrofuran, cyclohexanone, butan-1-ol, butyronitrile, methyl isobutyl ketone, methyl ethyl ketone or acetone.

Using the procedures disclosed herein, compound (I) tosylate Form A can be reproducibly manufactured following small, intermediate or large scale synthesis.

In a further aspect, the present invention provides processes for the preparation of compound (I) tosylate Form A.

Thus, in one aspect, the invention provides a process for the preparation of compound (I) tosylate Form A comprising crystallisation or recrystallisation from a solvent selected from acetonitrile, tetrahydrofuran, cyclohexanone, butan-1-ol, butyronitrile, methyl isobutyl ketone, methyl ethyl ketone and acetone. In another aspect, the invention provides a process for the preparation of compound (I) tosylate Form A comprising crystallisation or recrystallisation from acetonitrile, tetrahydrofuran or acetone. In another aspect, the invention provides a process for the preparation of compound (I) tosylate Form A comprising crystallisation or recrystallisation from acetonitrile.

The crystallisation or recrystallisation of compound (I) tosylate Form A may be performed by forming a supersaturated solution of the compound (I) tosylate from the solvent. Supersaturation may be achieved by, for example, concentrating the solution by removing solvent, cooling the solution or adding a suitable anti-solvent. When crystallisation is initiated by concentrating the solution, the solvent may be removed using well known methods such as evaporation or distillation. Crystallisation or recrystallisation may also be promoted by seeding the solution with compound (I) tosylate Form A crystals.

The compound (I) tosylate salt is conveniently prepared in-situ by reacting p-toluenesulfonic acid with a solution of compound (I) in one of the above mentioned solvents. The molar ratio of compound (I) to p-toluenesulfonic acid is suitably about 1:1. Following reaction with the p-toluenesulfonic acid, the compound (I) tosylate form A is crystallised from the solvent system as described herein.

When the compound (I) tosylate Form A is recrystallised, from one of the above solvents, compound (I) tosylate Form A is dissolved in the solvent and is then crystallised from solution as described herein. Recrystallisation may be useful for purifying the salt, improving the degree of crystallinity or improving the morphology of the compound (I) tosylate Form A crystals.

In another aspect, the invention provides a process for the preparation of compound (I) tosylate Form A comprising the following steps:

i) heating compound (I) in acetonitrile to obtain a solution;
ii) adding a p-toluenesulfonic acid to the solution in step i);
iii) cooling the reaction mixture to effect crystallisation; and
iv) collecting and drying the compound (I) tosylate Form A.

As will be realised step i) of the process provides a solution of compound (I) in acetonitrile. The solution may be obtained by dissolving any form of compound (I) into the acetonitrile. For example the starting form of compound (I) free-base could be crystalline, semi-crystalline or amorphous. Suitably, the compound (I) is dissolved in the acetonitrile by heating the mixture. Conveniently, the mixture in step i) is heated to a temperature about 50° C. or above, for example from about 50° C. to the reflux temperature, suitably from 50° C. to about 80° C., conveniently about 80° C.

In step ii) the p-toluenesulfonic acid may be added to the solution in any convenient form, for example as a solid or conveniently as a solution. The p-toluenesulfonic acid may be used in the anhydrous form or as the monohydrate. Conveniently, the p-toluenesulfonic acid is added to the solution in step i) as a solution of the acid in acetonitrile. When a solution of the acid in acetonitrile is used, it may be added to the solution in step i) at ambient temperature or as a hot solution. If the acid solution is added hot to the solution in step i), the acid solution may be at a temperature similar to that used in step i), for example from 50° C. to about 80° C. Conveniently the solution of p-toluenesulfonic acid in acetonitrile is at ambient temperature when it is added to the solution of step i). The molar ratio of compound (I) to p-toluenesulfonic acid is about 1:1. Following addition of the p-toluenesulfonic acid, the reaction mixture is allowed to stand, suitably with stirring to allow the acid to react with compound (I). The p-toluenesulfonic acid may be added to the solution of compound (I). However, the solution of compound (I) could also be added to the p-toluenesulfonic acid.

In step iii) the reaction mixture is cooled to effect crystallisation of the compound (I) tosylate. Suitably the reaction mixture is cooled to about 20° C., or less. In one embodiment the reaction mixture in step iii) is cooled to about 5° C. In one embodiment of the process the reaction mixture is cooled to about 5° C. and then re-heated to about 80° C., the cooling and re-heating may be repeated a number of times, for example 1, 2, 3, or 4 cycles of cooling and reheating before the final cooling and crystallisation of the compound (I) tosylate Form A. The temperature cycling may improve the physical form of the crystalline material and improve, for example, the material handling properties of the compound (I) tosylate Form A during subsequent processing. For example, subsequent formulation into a pharmaceutically acceptable composition such as a tablet or capsule.

In step iv) of the process the compound (I) tosylate Form A may be collected by conventional methods, for example by filtration. Following collection the compound (I) tosylate Form A is optionally washed with acetonitrile and may be dried. Conveniently the compound (I) tosylate Form A is dried under vacuum at a temperature of about 50° C.

The compound (I) tosylate Form A is suitably milled prior to formulation. The milling may be carried out using conventional methods, for example by wet milling to give a reproducible physical form and particle size prior to further processing of the compound (I) tosylate Form A. Conveniently, the compound (I) tosylate Form A is wet milled in-situ following crystallisation in step iii) of the process. The wet milling may be performed using, for example an in-line rotor-stator mill.

In a further aspect, the present invention provides compound (I) tosylate, or a Form thereof described herein for use in therapy.

In a further aspect, the present invention provides compound (I) tosylate, or a Form thereof described herein for use in the manufacture of a medicament for the treatment or prophylaxis of diseases or conditions in which inhibition of neutrophil elastase activity is beneficial.

In a further aspect, the present invention provides a method of treatment or prophylaxis of a disease or condition mediated by neutrophil elastase activity comprising administering to a patient in need thereof a therapeutically effective amount of compound (I) tosylate, or a Form thereof described herein.

In a further aspect, the present invention provides compound (I) tosylate, or a Form thereof described herein for the treatment of diseases or conditions in which inhibition of neutrophil elastase activity is beneficial.

In a further aspect, the present invention provides a pharmaceutical composition comprising compound (I) tosylate Form A. Suitably the pharmaceutical composition comprises compound (I) tosylate Form A and a pharmaceutically acceptable adjuvant, diluent or carrier.

In a further aspect, the present invention provides a method of treating a disease or condition mediated by neutrophil elastase activity, comprising administering to a patient in need thereof a therapeutically effective amount of a pharmaceutical composition comprising compound (I) tosylate Form A.

In a further aspect, the present invention provides the use of a pharmaceutical composition comprising compound (I) tosylate Form A for the treatment of a disease or condition in which inhibition of neutrophil elastase activity is beneficial.

In another aspect, the invention provides the use of a pharmaceutical composition comprising compound (I) tosylate Form A in the manufacture of a medicament for the treatment or prophylaxis of inflammatory diseases or conditions.

In another aspect of the invention there is provided a method of treating, or reducing the risk of, inflammatory diseases or conditions which comprises administering to a person suffering from or at risk of, said disease or condition, a therapeutically effective amount of a pharmaceutical composition comprising compound (I) tosylate Form A.

In another aspect of the invention there is provided compound (I) tosylate Form A for the treatment or prophylaxis of inflammatory diseases or conditions.

Compound (I) tosylate and the Forms described herein can be used in the treatment of diseases of the respiratory tract such as obstructive diseases of the airways including: asthma, including bronchial, allergic, intrinsic, extrinsic, exerciseinduced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

Compound (I) tosylate and the Forms described herein can also be used in the treatment of diseases of bone and joints such as arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies.

Compound (I) tosylate and the Forms described herein can also be used in the treatment of pain and connective tissue remodelling of musculoskeletal disorders due to injury [for example, sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis).

Compound (I) tosylate and the Forms described herein can also be used in the treatment of diseases of skin such as psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme, both infective and non-infective; panniculitis; cutaneous lymphomas, non-melanoma skin cancer and other dysplastic lesions; drug-induced disorders including fixed drug eruptions.

Compound (I) tosylate and the Forms described herein can also be used in the treatment of diseases of the eye such as blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial.

Compound (I) tosylate and the Forms described herein can also be used in the treatment of diseases of the gastrointestinal tract such as glossitis, gingivitis, periodontitis; oesophagitis, including reflux; eosinophilic gastro-enteritis, mastocytosis, Crohn's disease, colitis including ulcerative colitis, proctitis, pruritis ani, irritable bowel syndrome, non-inflammatory diarrhoea, and food-related allergies which may have effects remote from the gut (for example, migraine, rhinitis or eczema).

Compound (I) tosylate and the Forms described herein can also be used in the treatment of diseases of the cardiovascular system such as atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins.

Compound (I) tosylate and the Forms described herein can also be used in oncology such as in the treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

In particular, compound (I) tosylate and the Forms described herein may be used in the treatment of adult respiratory distress syndrome (ARDS), cystic fibrosis, pulmonary emphysema, chronic obstructive pulmonary disease (COPD), pulmonary hypertension, asthma, rhinitis, ischemia-reperfusion injury, rheumatoid arthritis, osteoarthritis, cancer, atherosclerosis and gastric mucosal injury.

More particularly, compound (I) tosylate and the Forms described herein may be used in the treatment of chronic obstructive pulmonary disease (COPD), cystic fibrosis, bronchiectasis, asthma and rhinitis.

In one aspect, compound (I) tosylate and the Forms described herein may be used in the treatment of chronic obstructive pulmonary disease (COPD).

In one aspect, compound (I) tosylate and the Forms described herein may be used in the treatment of cystic fibrosis.

In one aspect, compound (I) tosylate and the Forms described herein may be used in the treatment of bronchiectasis.

Thus, the invention provides the use of a compound (I) tosylate Form A in the manufacture of a medicament for the treatment or prophylaxis of chronic obstructive pulmonary disease (COPD).

In another aspect of the invention there is provided a method of treatment or prophylaxis of chronic obstructive pulmonary disease (COPD) comprising administering to a patient in need thereof a therapeutically effective amount of compound (I) tosylate, or a Form thereof described herein.

In another aspect of the invention there is provided a method of treatment or prophylaxis of bronchiectasis comprising administering to a patient in need thereof a therapeutically effective amount of compound (I) tosylate, or a Form thereof described herein.

In another aspect of the invention there is provided a method of treatment or prophylaxis of cystic fibrosis comprising administering to a patient in need thereof a therapeutically effective amount of compound (I) tosylate, or a Form thereof described herein.

Thus, the invention provides the use of a compound (I) tosylate Form A in the manufacture of a medicament for the treatment or prophylaxis of cystic fibrosis.

Thus, the invention provides the use of a compound (I) tosylate Form A in the manufacture of a medicament for the treatment or prophylaxis of bronchiectasis.

Thus, the invention provides compound (I) tosylate, or a Form thereof described herein, for use in the treatment or prophylaxis of COPD.

Thus, the invention provides compound (I) tosylate, or a Form thereof described herein, for use in the treatment or prophylaxis of cystic fibrosis.

Thus, the invention provides compound (I) tosylate, or a Form thereof described herein, for use in the treatment or prophylaxis of bronchiectasis.

Compound (I) tosylate and the Forms thereof described herein may be particularly suitable for use in the treatment of COPD, including the treatment or prophylaxis of symptoms of COPD. Such symptoms include one or more of, dyspnea (breathlessness or shortness of breath), decreased exercise capacity, chronic cough, wheezing or excessive sputum production.

Accordingly, in another aspect of the invention there is provided a method for the reduction of symptoms of COPD (including chronic bronchitis and emphysema) in a patient, comprising administering to a patient in need thereof a therapeutically effective amount of compound (I) tosylate, or a Form thereof described herein.

Patients with COPD often experience exacerbations of the condition, resulting in an acute increase in disease symptoms. Such exacerbations are often caused by infection of the tracheobronchial tree or air pollution, however, in many patients the cause of exacerbations is unknown. Exacerbations are a poor prognostic factor for disease progression and patients with exacerbations often require hospitalisation. Exacerbations can result in a permanent reduction in lung function and a worsening of symptoms. There is therefore a need to find suitable methods for preventing or treating such exacerbations. Compound (I) tosylate, or a Form thereof described herein, may be useful for the treatment or prophylaxis of COPD exacerbations. Accordingly compound (I) tosylate, or a Form thereof described herein, may be useful for treating the severity, frequency and/or duration of COPD exacerbations.

Accordingly, in another aspect of the invention there is provided a method for the reduction of severity, frequency and/or duration of exacerbations in a patient with COPD (including chronic bronchitis and emphysema) comprising administering to a patient in need thereof a therapeutically effective amount of compound (I) tosylate, or a Form thereof described herein.

Compound (I) tosylate, or a Form thereof described herein, may also be useful in stabilising or slowing down disease progression of COPD and may provide a disease modifying effect on COPD. Such disease modification may provide a sustained improvement in lung function and/or lung structure.

The compound (I) tosylate may be used alone or may be administered together with other treatments for the medical conditions described herein. For example the compound (I) tosylate may be used as an adjunctive treatment in addition to other treatments of a condition such as COPD. For example, compound (I) tosylate may be administered in conjunction with a second active ingredient selected from one or more of:
(i) antioxidants:—Allopurinol, Erdosteine, Mannitol, N-acetyl cysteine choline ester, N-acetyl cysteine ethyl ester, N-Acetylcysteine, N-Acetylcysteine amide and Niacin;
(ii) chemokine antagonists:—BX471 ((2R)-1-[[2-[(aminocarbonyl)amino]-4-chlorophenoxy]acetyl]-4-[(4-fluorophenyl)methyl]-2-methylpiperazine monohydrochloride), CCX634, N-{2-[(2S)-3-{[1-(4-chlorobenzyl) piperidin-4-yl]amino}-2-hydroxy-2-methylpropyl] oxy]-4-hydroxyphenyl}acetamide (see WO 2003/051839), and 2-{2-Chloro-5-{[(2S)-3-(5-chloro-1'H, 3H-spiro[1-benzofuran-2,4'-piperidin]-1'-yl)-2-hydroxypropyl]oxy}-4-[(methylamino)carbonyl] phenoxy}-2-methylpropanoic acid (see WO 2008/010765), 656933 (N-(2-bromophenyl)-N'-(4-cyano-1H-1,2,3-benzotriazol-7-yl)urea), 766994 (4-({[({[(2R)-4-(3,4-dichlorobenzyl)morpholin-2-yl] methyl}amino)carbonyl]-amino}methyl)benzamide), CCX-282, CCX-915, Cyanovirin N, E-921, INCB-003284, INCB-9471, Maraviroc, MLN-3701, MLN-3897, T-487 (N-{1-[3-(4-ethoxyphenyl)-4-oxo-3,4-dihydropyrido[2,3-d]pyrimidin-2-yl]ethyl}-N-(pyridin-3-ylmethyl)-2-[4-(trifluoromethoxy)phenyl]acetamide) and Vicriviroc
(iii) Corticosteroids:—Alclometasone dipropionate, Amelometasone, Beclomethasone dipropionate, Budesonide, Butixocort propionate, Ciclesonide, Clobetasol propionate, Desisobutyrylciclesonide, Etiprednol dicloacetate, Fluocinolone acetonide, Fluticasone Furoate, Fluticasone propionate, Loteprednol etabonate (topical) and Mometasone furoate.
(iv) DP1 antagonisits:—L888839 and MK0525;
(v) Histone deacetylase inducers:—ADC4022, Aminophylline, a Methylxanthine or Theophylline;
(vi) IKK2 inhibitors:—2-{[2-(2-Methylamino-pyrimidin-4-yl)-1H-indole-5-carbonyl]-amino}-3-(phenyl-pyridin-2-yl-amino)-propionic acid;
(vii) COX inhibitors:—Celecoxib, Diclofenac sodium, Etodolac, Ibuprofen, Indomethacin, Meloxicam, Nimesulide, OC1768, OC2125, OC2184, OC499, OCD9101, Parecoxib sodium, Piceatannol, Piroxicam, Rofecoxib and Valdecoxib;
(viii) Lipoxygenase inhibitors:—Ajulemic acid, Darbufelone, Darbufelone mesilate, Dexibuprofen lysine (monohydrate), Etalocib sodium, Licofelone, Linazolast, Lonapalene, Masoprocol, MN-001, Tepoxalin, UCB-35440, Veliflapon, ZD-2138, ZD-4007 and Zileuton ((±)-1-(1-Benzo[b]thien-2-ylethyl)-1-hydroxyurea);
(ix) Leukotriene receptor antagonists:—Ablukast, Iralukast (CGP 45715A), Montelukast, Montelukast sodium, Ontazolast, Pranlukast, Pranlukast hydrate (mono Na salt), Verlukast (MK-679) and Zafirlukast;

(x) MPO Inhibitors:—Hydroxamic acid derivative (N-(4-chloro-2-methyl-phenyl)-4-phenyl-4-[[(4-propan-2-ylphenyl)sulfonylamino]methyl]piperidine-1-carboxamide), Piceatannol and Resveratrol;

(xi) Beta2-adrenoceptor agonists:—metaproterenol, isoproterenol, isoprenaline, albuterol, salbutamol (e.g. as sulfate), formoterol (e.g. as fumarate), salmeterol (e.g. as xinafoate), terbutaline, orciprenaline, bitolterol (e.g. as mesylate), pirbuterol, salmeterol (e.g. as xinafoate), bambuterol (e.g. as hydrochloride), carmoterol, indacaterol (CAS no 312753-06-3; QAB-149), formanilide derivatives e.g. 3-(4-{[6-({(2R)-2-[3-(formylamino)-4-hydroxyphenyl]-2-hydroxyethyl}amino)hexyl]oxy}-butyl)-benzenesulfonamide; 3-(4-{[6-({(2R)-2-hydroxy-2-[4-hydroxy-3-(hydroxy-methyl)phenyl]ethyl}amino)-hexyl]oxy}butyl)benzenesulfonamide; GSK 159797, GSK 159802, GSK 597901, GSK 642444, GSK 678007; and a compound selected from N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide, N-[2-(Diethylamino)ethyl]-N-(2-{[2-(4-hydroxy-2-oxo-2,3-dihydro-1,3-benzothiazol-7-yl)ethyl]amino}ethyl)-3-[2-(3-chlorophenyl)ethoxy]propanamide, 7-[(1R)-2-({2-[(3-{[2-(2-Chlorophenyl)ethyl]amino}propyl)thio]ethyl}amino)-1-hydroxyethyl]-4-hydroxy-1,3-benzothiazol-2(3H)-one, and N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. wherein the counter ion is hydrochloride (for example a monohydrochloride or a dihydrochloride), hydrobromide (for example a monohydrobromide or a dihydrobromide), fumarate, methanesulfonate, ethanesulfonate, benzenesulfonate, 2,5-dichlorobenzenesulfonate, p-toluenesulfonate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), D-mandelate, L-mandelate, cinnamate or benzoate.). For example N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide e.g. dihydrobromide as described in WO 2008/096111 or N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide e.g. di-D-mandelate salt as described in WO 2008/075026.

(xii) Muscarinic receptor (M1, M2, and M3) antagonists:—Aclidinium bromide, Glycopyrrolate (such as R,R-, R,S-, S,R-, or S,S-glycopyrronium bromide), Oxitropium bromide, Pirenzepine, telenzepine, Tiotropium bromide, 3(R)-1-phenethyl-3-(9H-xanthene-9-carbonyloxy)-1-azoniabicyclo[2.2.2]octane bromide, (3R)-3-[(2S)-2-cyclopentyl-2-hydroxy-2-thien-2-ylacetoxy]-1-(2-phenoxyethyl)-1-azoniabicyclo[2.2.2]actane bromide, a quaternary salt (such as [2-((R)-Cyclohexyl-hydroxy-phenyl-methyl)-oxazol-5-ylmethyl]-dimethyl-(3-phenoxy-propyl)-ammonium salt, [2-(4-Chloro-benzyloxy)-ethyl]-[2-((R)-cyclohexyl-hydroxy-phenyl-methyl)-oxazol-5-ylmethyl]-dimethyl-ammonium salt and (R)-1-[2-(4-fluoro-phenyl)-ethyl]-3-((S)-2-phenyl-2-piperidin-1-yl-propionyloxy)-1-azonia-bicyclo[2.2.2]octane salt wherein the counter-ion is, for example, chloride, bromide, sulfate, methanesulfonate, benzenesulfonate (besylate), toluenesulfonate (tosylate), napthalenebissulfonate (napadisylate or hemi-napadisylate), phosphate, acetate, citrate, lactate, tartrate, mesylate, maleate, fumarate or succinate) as described in for example WO2008/075005 and WO2009/154554. Another muscarinic receptor antagonist is ((R)-3-(1-phenyl-cycloheptanecarbonyloxy)-1-(pyridin-2-ylcarbamoylmethyl)-1-azonia-bicyclo[2.2.2]octane salts described in WO2008/059245, including the salt described in WO2009/138707 e.g. ((R)-3-(1-phenyl-cycloheptanecarbonyloxy)-1-(pyridin-2-ylcarbamoylmethyl)-1-azonia-bicyclo[2.2.2]octane bromide. Another muscarinic receptor antagonist is [2-(4-chloro-benzyloxy)-ethyl]-[2-((R)-cyclohexyl-hydroxy-phenyl-methyl)-oxazol-5-ylmethyl]-dimethyl-ammonium salt, e.g. methane sulfonate as described in WO 2007/017669, or hemi-naphthalene-1,5-bissulfonate as described in WO 2008/096149. Another muscarinic receptor antagonist is (R)-1-[3-(cyclohexyl-hydroxy-phenyl-methyl)-isoxazol-5-ylmethyl]-3-(3-fluoro-phenoxy)-1-azonia-bicyclo[2.2.]octane salt, e.g. chloride as described in WO 2008/099186. A further muscarinic receptor antagonist is anti-(1S,2R) 2-(9-hydroxy-9H-xanthene-9-carbonyloxy)-bicyclo[2.2.1]hept-7-yl]-dimethyl-(3-phenoxy-propyl)-ammonium salt, e.g. bromide as described in WO 2007/017670.

(xiii) p38 Inhibitors:—681323, 856553, AMG548 (2-[[(2S)-2-amino-3-phenylpropyl]amino]-3-methyl-5-(2-naphthalenyl)-6-(4-pyridinyl)-4(3H)-pyrimidinone), Array-797, AZD6703, Doramapimod, KC-706, PH 797804, R1503, SC-80036, SCIO469, 6-chloro-5-[[(2S,5R)-4-[(4-fluorophenyl)methyl]-2,5-domethyl-1-piperazinyl]carbonyl]-N,N,1-trimethyl-α-oxo-1H-indole-3-acetamide, VX702, VX745 (5-(2,6-dichlorophenyl)-2-(phenylthio)-6H-pyrimido[1,6-b]pyridazin-6-one), and N-cyclopropyl-3-fluoro-4-methyl-5-[3-[[1-[2-[2-(methylamino)ethoxy]phenyl]cyclopropyl]amino]-2-oxo-1(2H)-pyrazinyl]-benzamide e.g. base form as described in WO2009/001132;

(xiv) PDE4 Inhibitors:—256066, Arofylline (3-(4-chlorophenyl)-3,7-dihydro-1-propyl-1H-Purine-2,6-dione), AWD 12-281 (N-(3,5-dichloro-4-pyridinyl)-1-[(4-fluorophenyl)methyl]-5-hydroxy-α-oxo-1H-indole-3-acetamide), BAY19-8004 (Bayer), CDC-801 (Calgene), Celgene compound (((βR)-β-(3,4-dimethoxyphenyl)-1,3-dihydro-1-oxo-2H-isoindole-2-propanamide), Cilomilast (cis-4-cyano-4-[3-(cyclopentyloxy)-4-methoxyphenyl]-cyclohexanecarboxylic acid), 2-(3,5-dichloro-4-pyridinyl)-1-(7-methoxyspiro[1,3-benzodioxole-2,1'-cyclopentan]-4-yl)ethanone (CAS number 185406-34-2)), (2-(3,4-difluorophenoxy)-5-fluoro-N—[cis-4-[(2-hydroxy-5-methylbenzoyl)amino]cyclohexyl]-)-3-pyridinecarboxamide), (2-(3,4-difluorophenoxy)-5-fluoro-N—[cis-4-[[2-hydroxy-5-(hydroxymethyl)benzoyl]amino]cyclohexyl]-3-pyridinecarboxamide,), CT2820, GPD-1116, Ibudilast, IC 485, KF 31334, KW-4490, Lirimilast ([2-(2,4-dichlorobenzoyl)-6-[(methylsulfonyl)oxy]-3-benzofuranyl])-urea), (N-cyclopropyl-1,4-dihydro-4-oxo-1-[3-(3-pyridinylethynyl)phenyl]-)-1,8-naphthyridine-3-carboxamide), (N-(3,5-dichloro-4-pyridinyl)-4-(difluoromethoxy)-8-[(methylsulfonyl)amino])-1-dibenzofurancarboxamide), ONO6126, ORG 20241 (4-(3,4-dimethoxyphenyl)—N-hydroxy-)-2-thiazolecarboximidamide), PD189659/PD168787

(Parke-Davis), Pentoxifylline (3,7-dihydro-3,7-dimethyl-1-(5-oxohexyl)-)-1H-purine-2,6-dione), compound (5-fluoro-N-[4-[(2-hydroxy-4-methyl-benzoyl)amino]cyclohexyl]-2-(thian-4-yloxy)pyridine-3-carboxamide), Piclamilast (3-(cyclopentyloxy)-N-(3,5-dichloro-4-pyridinyl)-4-methoxy-benzamide), PLX-369 (WO 2006026754), Roflumilast (3-(cyclopropylmethoxy)-N-(3,5-dichloro-4-pyridinyl)-4-(difluoromethoxy)benzamide), SCH 351591 (N-(3,5-dichloro-1-oxido-4-pyridinyl)-8-methoxy-2-(trifluoromethyl)-5-quinolinecarboxamide), SelCID™ CC-10004 (Calgene), T-440 (Tanabe), Tetomilast (6-[2-(3,4-diethoxyphenyl)-4-thiazolyl]-2-pyridinecarboxylic acid), Tofimilast (9-cyclopentyl-7-ethyl-6,9-dihydro-3-(2-thienyl)-5H-pyrazolo[3,4-c]-1,2,4-triazolo[4,3-a]pyridine), TPI 1100, UCB 101333-3 (N,2-dicyclopropyl-6-(hexahydro-1H-azepin-1-yl)-5-methyl-4-pyrimidinamine), V-11294A (Napp), VM554/VM565 (Vernalis), Zardaverine (6-[4-(difluoromethoxy)-3-methoxyphenyl]-3(2H)-pyridazinone) and 6-fluoro-N-((1s,4s)-4-(6-fluoro-2,4-dioxo-1-(4'-(piperazin-1-ylmethyl)-biphenyl-3-yl)-1,2-dihydropyrido[2,3-d]pyrimidin-3(4H)-yl)cyclohexyl)imidazo[1,2-a]pyridine-2-carboxamide, or a salt thereof (as disclosed in, for example WO2008084223).

(xv) PDE5 Inhibitors:—Gamma-glutamyl[s-(2-iodobenzyl)cysteinyl]glycine, Tadalafil, Vardenafil, sildenafil, 4-phenyl-methylamino-6-chloro-2-(1-imidazolyl)-quinazoline, 4-phenyl-methylamino-6-chloro-2-(3-pyridyl)-quinazoline, 1,3-dimethyl-6-(2-propoxy-5-methanesulfonylamidophenyl)-1,5-dihydropyrazolo[3,4-d]pyrimidin-4-one and 1-cyclopentyl-3-ethyl-6-(3-ethoxy-4-pyridyl)-pyrazolo[3,4-d]pyrimidin-4-one;

(xvi) PPARγ agonists:—Pioglitazone, Pioglitazone hydrochloride, Rosiglitazone Maleate, Rosiglitazone Maleate ((−)-enantiomer, free base), Rosiglitazone maleate/Metformin hydrochloride and Tesaglitizar;

(xvii) Protease Inhibitors:—Alpha1-antitrypsin proteinase Inhibitor, EPI-HNE4, UT-77, ZD-0892, DPC-333, Sch-709156 and Doxycycline;

(xviii) Statins:—Atorvastatin, Lovastatin, Pravastatin, Rosuvastatin and Simvastatin (xix) Thromboxane Antagonists: Ramatroban and Seratrodast;

(xx) Vasodilators:—A-306552, Ambrisentan, Avosentan, BMS-248360, BMS-346567, BMS-465149, BMS-509701, Bosentan, BSF-302146 (Ambrisentan), Calcitonin Gene-related Peptide, Daglutril, Darusentan, Fandosentan potassium, Fasudil, Iloprost, KC-12615 (Daglutril), KC-12792 2AB (Daglutril), Liposomal treprostinil, PS-433540, Sitaxsentan sodium, Sodium Ferulate, TBC-11241 (Sitaxsentan), TBC-3214 (N-(2-acetyl-4,6-dimethylphenyl)-3-[[(4-chloro-3-methyl-5-isoxazolyl)amino]sulfonyl]-2-thiophenecarboxamide), TBC-3711, Trapidil, Treprostinil diethanolamine and Treprostinil sodium;

(xxi) ENACs:—Amiloride, Benzamil, Triamterene, 552-02, PSA14984, PSA25569, PSA23682 and AER002;

(xxii) Antimicrobials:—aminopenicillins, macrolides and tetracyclines; and (xxiii) a dual muscarinic receptor antagonist/β$_2$ adrenoceptor agonist (MABA compound—a compound having dual activity as both a muscarinic antagonist and as a β$_2$-adrenoceptor agonist), for example a MABA is a compound disclosed in: WO2004089892, WO2004106333, US20040167167, WO2005111004, WO2005051946, US20050256114, WO2006023457, WO2006023460, US20060223858, US20060223859, WO2007107828, WO2008000483, U.S. Pat. No. 7,317, 102 or WO2008041095. Particular compounds include those described by Ray et al, Expert Opinion on Therapeutic Patents, January 2009, Vol. 19, No. 1, Pages 1-12, GSK961081 or (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one or a salt thereof as described in WO2009/098448.

The compound (I) tosylate and the second active ingredient(s) may be administered sequentially, substantially simultaneously or separately. Where the compound (I) tosylate and second active ingredient(s) are administered separately, the time period between administrations of the active ingredient(s) should be sufficiently short that the therapeutic benefit of the first active is not lost before administration of the further active ingredient(s). For substantially simultaneous administration the compound (I) tosylate could be administered as a combined dosage where the actives are administered together. However, conveniently, the actives may be administered in separate dosage forms close together. The active ingredients may be administered to a patient by the same or different route and in any order. For example compound (I) tosylate may be administered orally, and the second active ingredient by inhalation. Compound (I) tosylate may be particularly suitable as an adjunctive therapy, wherein a patient is or has been treated with one or more second active ingredients(s) as a primary therapy and is treated with compound (I) tosylate to treat ongoing symptoms or conditions that are not adequately controlled or treated by the primary therapy.

By way of example, compound (I) tosylate could be used in the treatment of a patient with COPD, in conjunction (for example as an adjunctive treatment) with one or more second active ingredient selected from:

a) a (β$_2$-adrenoceptor agonist;
b) a corticosteroid;
c) a muscarinic antagonist;
d) a dual muscarinic receptor antagonist/β$_2$ adrenoceptor agonist (MABA compound); and
e) a PDE4 inhibitor.

Examples of such second active ingredients a) to e) include those hereinbefore described. For example, in addition to the compound (I) tosylate a patient may be treated with a beta2-adrenoceptor agonist and a corticosteroid combination such as Symbicort® or Advair®. Alternatively the patient may be treated with a β$_2$-adrenoceptor agonist, a corticosteroid and a muscarinic agent in addition to the compound (I) tosylate.

Accordingly, in another aspect of the invention there is provided an adjunctive maintenance treatment for the reduction of severity, frequency and/or duration of exacerbations in a patient with COPD (including chronic bronchitis and emphysema), who is symptomatic on existing therapy, which method comprising administering to said patient a therapeutically effective amount of compound (I) tosylate, or a Form thereof described herein.

In another aspect of the invention there is provided adjunctive maintenance treatment for the reduction of symptoms in a patient with COPD (including chronic bronchitis and emphysema) who is symptomatic on existing therapy, which method comprising administering to said patient a therapeutically effective amount of compound (I) tosylate, or a Form thereof described herein.

In another aspect of the invention there is provided adjunctive maintenance treatment for the reduction of severity, frequency and/or duration of exacerbations and/or reduction of symptoms with in a patient with COPD (including chronic bronchitis and emphysema), who is symptomatic on existing therapy, which method comprising administering to said patient a therapeutically effective amount of compound (I) tosylate, or a Form thereof described herein.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dose of the compound to be administered will depend on the disease being treated, the severity of the disease, the mode of administration, the age, weight and sex of the patient. Such factors may be determined by the attending physician. However, in general, satisfactory results are obtained when the compounds are administered to a human at a daily dosage of between 0.1 mg/kg to 100 mg/kg (measured as the active ingredient).

Suitably the daily dose of compound (I) is from 0.5 to 200 mg per day, for example from 2.5 to 120 mg per day. For example the daily dose of compound (I) is 0.5, 1, 2.5, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 mg per day. The dose of compound (I) may be administered as a single dose or as a divided dose, for example wherein the total daily dose is divided in to two or more fractions, which administered during the day. In a particular embodiment the compound (I) tosylate is administered twice a day (BID dosing). In a further embodiment the compound (I) tosylate is administered twice a day, wherein each dose is equivalent to from 5 mg to 60 mg of the compound (I) free base. For example 5 mg twice a day, 10 mg twice a day, 20 mg twice a day, 30 mg twice a day, 40 mg twice a day, 50 mg twice a day, or 60 mg twice a day. The above references to the doses of compound (I) refer to the weight of compound (I) free base. Accordingly, the amount of compound (I) tosylate required to give the desired dose of compound (I) free base will be higher. For example a 10 mg dose of compound (I) free base will be equivalent to approximately 13.2 mg of the compound (I) tosylate.

Formulation

The crystalline compound (I) tosylate may be used alone when appropriate, or in the form of appropriate pharmaceutical composition comprising the compound of the invention in combination with a pharmaceutically acceptable diluent, adjuvant or carrier. Particularly preferred are compositions not containing material capable of causing an adverse reaction, for example, an allergic reaction.

According to the invention, there is provided a pharmaceutical composition comprising a compound (I) tosylate Form A in admixture with a pharmaceutically acceptable diluent or carrier. The compound (I) tosylate Form A is suitably used in a micronised or a milled form. The compound (I) tosylate is preferably less than 50% by weight and more preferably less than 30% by weight of the total composition weight in the compositions described herein (including the oral compositions described hereafter). For example, the compound (I) tosylate Form A is suitably present in the compositions herein (including the oral compositions described hereafter) at between 0.1% and 30% by weight, for example at 1%, 2.5% 5%, 7.5%, 10%, 15% or 20% by weight.

We also provide a method of preparation of such pharmaceutical compositions that comprises mixing the ingredients.

The compound according to the invention may be administered topically, for example, to the lungs and/or the airways, in the form of solutions, suspensions, HFA aerosols or dry powder formulations, for example, formulations in the inhaler device known as Turbuhaler®; or systemically, for example, by oral administration in the form of tablets, pills, capsules, solutions, suspensions, emulsions, syrups, powders or granules; or by parenteral (including intraperitoneal, intravenous, subcutaneous or intramuscular injection) administration, for example, in the form of sterile parenteral solutions or suspensions; or by rectal administration, for example, in the form of suppositories.

Dry powder formulations and pressurized HFA aerosols of the compound of the invention may be administered by oral or nasal inhalation. For inhalation, the compound is desirably finely divided. The finely divided compound preferably has a mass median diameter of less than 10 μm, and may be suspended in a propellant mixture with the assistance of a dispersant, such as a $C_8$-$C_{20}$ fatty acid or salt thereof, (for example, oleic acid), a bile salt, a lipid, an alkyl saccharide, a perfluorinated or polyethoxylated surfactant, or other pharmaceutically acceptable dispersant.

The compound of the invention may also be administered by means of a dry powder inhaler. The inhaler may be a single or a multi dose inhaler, and may be a breath actuated dry powder inhaler.

One possibility to prepare a formulation for inhalation is to mix the finely divided compound with a carrier substance, for example, a mono-, di- or polysaccharide, a sugar alcohol, or an other polyol. Suitable carriers are sugars, for example, lactose, glucose, raffinose, melezitose, lactitol, maltitol, trehalose, sucrose, mannitol and starch. Alternatively the finely divided compound may be coated by another substance. The powder mixture may also be dispensed into hard gelatine capsules, each containing the desired dose of the active compound.

Another possibility is to process the finely divided powder into spheres that break up during the inhalation procedure. This spheronized powder may be filled into the drug reservoir of a multidose inhaler, for example, that known as Turbuhaler® in which a dosing unit meters the desired dose which is then inhaled by the patient. With this system the active compound, with or without a carrier substance, is delivered to the patient.

Compositions for Oral Administration

For oral administration the compound (I) tosylate may, for example, be admixed with an adjuvant, diluent or a filler, for example, lactose, saccharose, sorbitol, mannitol, dibasic calcium phosphate (dicalcium phosphate) including hydrated and anhydrous forms; a starch, for example, potato starch, corn (maize) starch or amylopectin; a cellulose derivative such as microcrystalline cellulose (MCC) or silicified microcrystalline cellulose (SMCC) and the like. In some embodiments mixtures of these may be used. In one embodiment the compound (I) tosylate is not admixed with mannitol. In one embodiment, the quantity of hydrophilic celluloses, such as MCC in the complete formulation ranges between 50% and 98%.

These adjuvents, diluents and fillers are used in total in 60 to 98 parts, preferably in 70 to 95 parts, thereof per 100 parts of the solid formulation by weight. Examples of cellulose derivatives such as microcrystalline cellulose, include Avicel PH101, PH102, PH102 SCG, PH200, PH301, PH302, and PH-F20, Avicel RC-A591NF. An example of silicified microcrystalline cellulose products is ProSolv 90 HD, a mixture of MCC and colloidal silicon dioxide (manufactured by JRS Pharma). Examples of dibasic calcium phosphate dihydrate products are Calipharm D (from ThermoPhos), ICL D (from ICL Performance Products), Calstar (FMC Biopolymer), Di-Cafos (Chemische Fabrik Budenheim), DI-TAB (Innophos) and Emcompress (JRS Pharma LP). Examples of dibasic calcium phosphate anhydrate are ICL A (from ICL Performance Products), Fuji Calin (from Fuji Chemicals), A-TAB (Innophos), Di-Cafos AN (Chemische Fabrik Budenheim) and Emcompress Anhydrous (JRS Pharma LP). Examples of mannitol products is Pearlitol DC 300 and Pearlitol SD200 (manufactured by Roquette). An example of a lactose product is Pharmatose DCL 15 (manufactured by DMV).

A binder may be optionally used, for example, hydroxypropyl cellulose (HPC), hydroxypropylmethyl cellulose (HPMC), polyvinylpyrrolidone (PVP) or gelatine and 0.5 to 10 parts, preferably 1 to 4 parts, thereof is used per 100 parts of the solid pharmaceutical formulation by weight. An example of hydroxypropyl cellulose includes HPC LF. Examples of hydroxypropylmethyl cellulose include PVP K30 and PVP K90.

Disintegrating agents include for example, carmellose calcium, carboxymethyl starch sodium, croscarmellose sodium, crospovidone (crosslinked polyvinylpyrrolidone) and the like, and 0.5 to 15 parts, preferably 2 to 10 parts, thereof is used per 100 parts of the solid pharmaceutical formulation by weight. Disintegrating agents are exemplified by Kollidon CL (manufactured by BSAF).

Lubricants include magnesium stearate, calcium stearate, sucrose esters of fatty acids, sodium stearyl fumarate, stearic acid, polyethyleneglycol, wax, paraffin and the like. The amount of lubricant is between 0.05% and 5% and is preferably between 0.5% to 3.5%, wherein the % is by weight of the formulation.

Surfactants include sodium lauryl sulfate, polysorbate 80, hydrogenated oil, polyoxyethylene(160)polyoxypropylene (30)glycol, and the like. The amount of surfactant is less than 2%, suitably less than 1.5%, for example less than 1.1% wherein the % is by weight of the formulation.

The compound (I) tosylate according to the present invention is particularly suitable for oral administration. As described hereinbefore, compound (I) tosylate has favourable dissolution properties. However, due to the inherent properties of compound (I), we have found that salts of compound (I) are prone to dissociation in the presence of water. This may lead to the re-precipitation of compound (I) from solution in a less soluble form such as the poorly soluble free base of compound (I). We have also found that the amorphous free base of compound (I) may be prone to gelling and as such forms gel lumps with small surface area thereby further reducing its dissolution rate. Therefore, the formation of compound (I) free base gel during wetting may affect the availability of compound (I) for absorption in the GI tract. The dissociation of salts of compound (I) to the free base and the subsequent gelling may also be influenced by the initial dissolution of the compound from a pharmaceutical composition following oral administration to a patient. In particular, if the compound (I) tosylate is dissolved and dissociated it may form a gel and thereby compound (I) could be less available for absorption due to its lack of availability and possible re-precipitation in a form with low solubility.

For an instant release composition the dissolution of the active ingredient needs to be fast so that as much of the active as possible is dissolved in the stomach/upper GI tract. Suitably the dissolution rate should be greater than 65% within 30 minutes, preferably more than 75%, more preferably more than 80% and most preferably more than 85% (for example more than 90%) within 30 minutes after oral administration.

Unless stated otherwise, the dissolution rate for the formulations described below was determined in 900 ml of 0.1 M HCl and using USP dissolution apparatus 2 (paddle) at 75 rpm and 37° C. using a Zymark Multidose G3 system. Analysis was made by UV spectrophotometer with a detection wavelength of 337 nm.

We have found that compound (I) tosylate (79 mg corresponding to 60 mg of the free base of compound (I)) alone in a capsule only dissolved to less than approximately 65% within 30 minutes. The slow dissolution of the capsule formulation is thought to be attributed to dissociation of the compound (I) tosylate of compound (I) and concomitant gelation of the amorphous free base formed in the dissociation process.

Surprisingly we have found that certain formulations of compound (I) tosylate Form A including many of the tablet compositions described hereafter in the Examples, provide an improved dissolution rate and generally gave greater than about 80% dissolution of the compound (I) tosylate Form A within 30 minutes in the 0.1 M HCl dissolution medium described above.

Accordingly, as a further independent aspect of the invention there is provided a pharmaceutical composition comprising compound (I) tosylate Form A and an excipient selected from microcrystalline cellulose, spray dried mannitol, a starch, lactose and dibasic calcium phosphate. An example of spray dried mannitol is Perlitol® SD200 (manufactured by Roquette). The starch used in these embodiments is suitably corn starch, for example Starch 1500® partially pregelatinized corn starch (Colorcon). The lactose is suitably lactose monohydrate.

According to a further aspect of the invention there is provided a pharmaceutical composition comprising compound (I) tosylate Form A and an excipient selected from microcrystalline cellulose, a starch (for example corn starch as hereinbefore described), lactose (for example lactose monohydrate) and dibasic calcium phosphate.

According to a further aspect of the invention there is provided a pharmaceutical composition comprising compound (I) tosylate Form A, dibasic calcium phosphate and an excipient selected from microcrystalline cellulose, a starch (for example corn starch as hereinbefore described) and lactose.

According to a further aspect of the invention there is provided a pharmaceutical composition comprising compound (I) tosylate Form A, microcrystalline cellulose and dibasic calcium phosphate.

We have surprisingly found that the presence of dibasic calcium phosphate improves the chemical stability of the compound (I) tosylate in a composition compared to formulations prepared without dibasic calcium phosphate. Accordingly the compositions containing dibasic calcium phosphate are expected to be advantageous for compositions containing compound (I) tosylate, such as tablets for oral administration as a result of the improved chemical stability provided by the dibasic calcium phosphate.

Accordingly, as a further independent aspect of the invention there is provided a pharmaceutical composition comprising compound (I) tosylate Form A and dibasic calcium phosphate.

We have surprisingly found that the presence of dibasic calcium phosphate in certain compositions significantly increases the dissolution rate of the compound (I) tosylate Form A when the composition is administered to an acidic dissolution medium (for example in the stomach following oral administration).

Suitably the dibasic calcium phosphate in the compositions described herein is present in an amount of 40% or less, for example less than 20%, such as from 1 to 20% and particularly 1%, 2.5%, 5%, 7.5%, 10%, 12.5% or 15% of the total composition weight.

Suitably the weight ratio of compound (I) tosylate to dibasic calcium phosphate is from 10:1 to 1:10, for example 7:1 to 1:7, for example 5:1 to 1:5, for example about 3:1 to 1:3 or about 2:1 to 1:2. In a particular embodiment the weight ratio of compound (I) tosylate salt to dibasic calcium phosphate is about 1.5:1. In another embodiment the weight ratio of compound (I) tosylate salt to dibasic calcium phosphate is about 1:6. In another embodiment the weight ratio of compound (I) tosylate salt to dibasic calcium phosphate is about 2:1.

The dibasic calcium phosphate present in the compositions described herein may be used as an anhydrous form or a hydrated form, such as dibasic calcium phosphate dihydrate. Unless stated otherwise, a reference to "dibasic calcium phosphate" herein is intended to encompass both anhydrous and hydrated forms.

In one embodiment the compositions according to the invention use dibasic calcium phosphate dihydrate. In another embodiment the compositions according to the invention use anhydrous dibasic calcium phosphate.

Dibasic calcium phosphate is well known and readily available. Examples of dibasic calcium phosphate dihydrate and anhydrate products are as hereinbefore defined.

In addition to the compound (I) tosylate Form A and the dibasic calcium phosphate the composition according to the invention optionally contain one or more additional excipient(s).

For example, one or more adjuvent, diluent, filler, binder, disintegrant, lubricant or surfactant. Examples of such adjuvants, diluents, fillers, binders, disintegrants, lubricants and surfactants are as hereinbefore described in relation to the general oral formulations above.

According to another aspect of the present invention there is provided a pharmaceutical composition comprising compound (I) tosylate Form A, dibasic calcium phosphate and an insoluble cellulose or cellulose derivative (for example microcrystalline cellulose)

According to another aspect of the present invention there is provided a pharmaceutical composition comprising: compound (I) tosylate Form A; dibasic calcium phosphate; an insoluble cellulose derivative (for example microcrystalline cellulose); a disintegrant; a surfactant and a lubricant.

Suitable disintegrants, lubricants and surfactants are as hereinbefore described. For example a suitable disintegrant is crospovidone (cross-linked polyvinylpyrrolidone). A suitable surfactant is for example an anionic surfactant such as sodium lauryl sulfate. A suitable lubricant is for example sodium stearyl fumarate or magnesium stearate.

According to another aspect of the present invention there is provided a pharmaceutical composition comprising compound (I) tosylate Form A, microcrystalline cellulose and dibasic calcium phosphate.

According to another aspect of the present invention there is provided a pharmaceutical composition comprising compound (I) tosylate Form A, microcrystalline cellulose, dibasic calcium phosphate and crospovidone.

According to another aspect of the present invention there is provided a pharmaceutical composition comprising compound (I) tosylate Form A, microcrystalline cellulose, dibasic calcium phosphate, crospovidone and sodium stearyl fumarate.

According to another aspect of the present invention there is provided a pharmaceutical composition comprising compound (I) tosylate Form A microcrystalline cellulose, dibasic calcium phosphate, crospovidone and magnesium stearate.

According to another aspect of the present invention there is provided a pharmaceutical composition comprising compound (I) tosylate Form A, microcrystalline cellulose, dibasic calcium phosphate, crospovidone, sodium stearyl fumarate and sodium lauryl sulfate.

According to another aspect of the present invention there is provided a pharmaceutical composition comprising compound (I) tosylate Form A, microcrystalline cellulose, dibasic calcium phosphate, crospovidone, magnesium stearate and sodium lauryl sulfate.

According to another aspect of the present invention there is provided a pharmaceutical composition comprising:
a) 0.1 to 40 (for example 0.5 to 20 parts such as 0.5 to 15 parts or 0.5 to 10 parts, particularly about 0.8, 3.3 or 9.8 parts) compound (I) tosylate Form A;
b) 2 to 10 parts (for example about 5 parts) dibasic calcium phosphate (particularly dibasic calcium phosphate dihydrate);
c) 60 to 90 parts (for example about 75 to 90, such as about 79, 80, 85 or 88 parts) microcrystalline cellulose;
d) 2 to 10 parts (for example about 4 parts) of a disintegrant (for example crospovidone);
e) 0.1 to 2 parts (for example about 1 parts) of a surfactant (for example an anionic surfactant such as sodium lauryl sulfate); and
f) 0.1 to 3 parts (for example about 1 part or 1.5 parts) of a lubricant (for example sodium stearyl fumarate or magnesium stearate);
wherein all parts are parts by weight of the total composition and the sum of the parts a) to f)=100.

When this composition is prepared in the form of a tablet composition it may be coated with a suitable coating as herein described.

According to another aspect of the present invention there is provided a pharmaceutical composition comprising:
a) about 0.5 to 15 parts compound (I) tosylate Form A (for example 0.5 to 10 parts, such about 0.8, 3 or 9.8 parts);
b) about 5 parts dibasic calcium phosphate (particularly dibasic calcium phosphate dihydrate);
c) about 75 to 90 parts microcrystalline cellulose (for example about 79, 85 or 88 parts);
d) about 4 parts crospovidone;
e) about 1 part sodium lauryl sulfate; and
f) about 1 part or 1.5 parts sodium stearyl fumarate;
wherein all parts are parts by weight of the total composition and the sum of the parts a) to f)=100.

When this composition is prepared in the form of a tablet composition it may be coated with a suitable coating as herein described.

In the above two embodiment the sum of parts (a)+(b) (compound (I) tosylate form A)+(microcrystalline cellulose) is from about 85 to 90, for example about 85, 86, 87, 88, 89 or 90 and particularly about 87 to 89.

The term "about" in the above two embodiments is to be understood to refer to a variation of approximately +/−10%. Accordingly reference to about 10 parts is to be considered to encompass approximately 9 to 11 parts.

Figure 3:
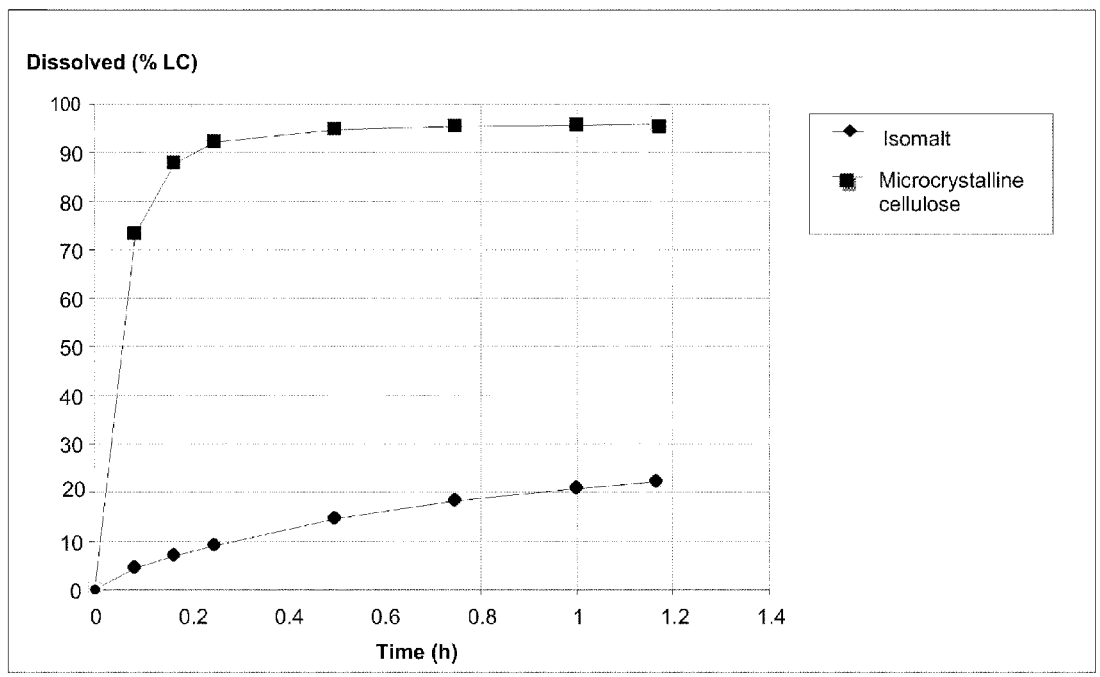
FIG. 3 shows the dissolution profile for the tablets prepared in Example 14; a tablet composition containing compound (I) tosylate Form A and microcrystalline cellulose (square data points); and a tablet composition containing compound (I) tosylate Form A and Isomalt (diamond data points). The dissolution was measured at pH 6.8 as described in Example 14. The x-axis shows time (hours), the y-axis shows % dissolved compound (I) (as % label claim (% LC)).

In another aspect of the invention we have found that by using a slowly dissolving or practically insoluble adjuvent, diluent or filler, for example microcrystalline cellulose (MCC), together with an insoluble adjuvant, diluent or filler, for example dibasic calcium phosphate an increased dissolution rate of the active compound (I) tosylate was observed in a pH 6.8 dissolution medium (see FIG. 3 and Example 14). Dissolution was measured using a USP dissolution apparatus 2 (paddle) at 75 rpm and 37° C. in a Zymark Multidose G3 system, 0.05 M phosphate buffer at pH 6.8 in a dissolution volume of 900 ml. Suitably in this embodiment the dibasic calcium phosphate is present in an amount of less than 40%, more preferably less than 20%, of the total formulation weight.

In this embodiment the composition may contain a cellulose product such as Avicel together with an inorganic compound such as dibasic calcium phosphate as excipients and various other additives for production of general pharmaceutical preparations, in their respective suitable amounts, unless they interfere with the effect of the invention. Such additives include excipients, pH-modifiers, surfactants, and the like.

According to another aspect of the present invention there is provided a pharmaceutical composition comprising compound (I) tosylate Form A and microcrystalline cellulose.

A particular embodiment provides a pharmaceutical composition comprising compound (I) tosylate Form A; microcrystalline cellulose; a diluent (such as lactose monohydrate) and a disintegrant (such as crospovidone). This composition may also comprise additional excipients, for example selected from a surfactant, a lubricant and a film-coating as described herein. An example of a composition according to this embodiment is a pharmaceutical composition comprising:

a) 0.1 to 40 (for example 0.5 to 20 parts such as 0.5 to 15 parts or 0.5 to 10 parts, particularly about 0.8, 3.3 or 9.8 parts) compound (I) tosylate Form A;
b) 2 to 10 parts (for example about 5 parts) of microcrystalline cellulose;
c) 60 to 90 parts (for example about 75 to 90, such as about 78, 80, 85 or 88 parts, particularly about 78 parts) of a diluent (for example lactose, particularly lactose monohydrate);
d) 2 to 10 parts (for example about 4 parts) of a disintegrant (for example crospovidone);
e) 0.1 to 2 parts (for example about 1 parts) of a surfactant (for example an anionic surfactant such as sodium lauryl sulfate); and
f) 0.1 to 3 parts (for example about 2 parts) of a lubricant (for example sodium stearyl fumarate or magnesium stearate);

wherein all parts are parts by weight of the total composition and the sum of the parts a) to f)=100. When this composition is prepared in the form of a tablet composition it may be coated with a suitable coating as herein described.

In this embodiment the sum of parts (a)+(b) (compound (I) tosylate form A)+(the diluent such as lactose monohydrate) is from about 85 to 90, for example about 85, 86, 87, 88, 89 or 90 and particularly about 87 to 89.

Certain compositions containing the sugar alcohol Isomalt have been found to exhibit a slow dissolution rate (see FIG. 3 and Example 14). Accordingly, in an embodiment, the composition according to the invention does not contain a significant quantity (for example more than 30%, 20%, 10% or 5% by weight Isomalt). Particularly in this embodiment the composition does not contain any Isomalt.

The pharmaceutical compositions for oral administration are suitably instant release compositions. It is to be understood that "instant release composition" refers to a composition in which at least 65%, preferably at least 75% and more preferably at least 85% by weight of the compound (I) tosylate Form A dissolves within 30 minutes in 900 ml of 0.1 M HCl (pH 1) at 75 rpm and 37° C. using USP dissolution apparatus 2 (paddles, Hanson SR8Plus or equivalent) in a fully automated system, Zymark Multidose G3 (software version 2.10.72 or later); UV spectrophotometer (HP 8453 spectrophotometer or equivalent, analytical wavelength 337 nm).

The compositions for oral administration described above are suitably prepared as for example, a tablet or granule form. In one embodiment the pharmaceutical composition is a tablet, particularly an instant release tablet for oral administration. In another embodiment, the pharmaceutical composition is in the form of granules. The granules may for example be conveniently filled into capsules or sachets for oral administration.

If coated tablets are required, the cores, prepared as described above, may be coated with a conventional tablet coating. Suitable tablet coatings are well known and include for example a concentrated sugar solution which may contain, for example, gum, gelatine, talcum, titanium dioxide, iron oxide and the like. Alternatively, the tablet may be film coated with a suitable polymer dissolved in a readily volatile organic solvent or in an inorganic solvent, for example water, which may contain, for example, gum, gelatine, talcum, titanium dioxide, iron oxide and the like. In one embodiment a tablet is coated with a film coating comprising hydroxypropylmethyl cellulose (HPMC), a plasticiser such as polyethylene glycol (PEG) and optionally a colorant (for example a pigment such as titanium dioxide and/or a ferric oxide). The coating is suitably applied to the tablet as an aqueous suspension using conventional spray coating techniques. Suitably the tablet coating comprises 0.5 to 10% by weight of the composition, for example from 1 to 5% and particularly from 3 to 5% by weight.

Due to the water sensitivity of the compound (I) tosylate the pharmaceutical compositions described herein are suitably prepared using for example, direct compression or a dry granulation process such as roller compaction or slugging.

The ingredients and the active substance are mixed in a suitable mixer. The active substance may be added in the form of a pregranulate or a micronised or milled powder to the powder mixture to be used to compress tablets. Alternatively the active substance may be added to the powder mixture to be used to compress tablets as a premix containing the active substance or micronised or milled active substance or a pregranulate and a part or all of at least one of the adjuvant, diluent or carrier ingredients. Alternatively the powder mixture to be used to compress tablets may be produced by a mixing procedure that is followed by a dry granulation process. When the process of dry granulation is followed, the active substance may be added to the powder mixture to be granulated in the form of a pregranulate or a micronised or milled powder. Alternatively the active substance may be added to the powder mixture to be granulated as a premix containing the active substance or micronised or milled active substance or a pregranulate and a part or all of at least one of the adjuvant, carrier or diluent ingredients. A lubricant like sodium stearyl fumarate or magnesium stearate may be added to the powder mixture to be granulated before granulation. The powder mixture is granulated using commercially available equipment.

The mixture of ingredients is compressed into tablets with commercially available equipment (e.g. a Diaf™ 20, Korsch EK0 or XP1, Fette 1090) using flow regulating agents like colloidal silica and lubricating agents like talcum, sodium stearyl fumarate or magnesium stearate.

For the preparation of soft gelatine capsules, the compound may be admixed with, for example, a vegetable oil or polyethylene glycol. Hard gelatine capsules may contain granules of the compound using either the above mentioned excipients for tablets. Also liquid or semisolid formulations of the drug may be filled into hard gelatine capsules.

The dose of compound (I) tosylate in each tablet or capsule may be altered by changing the size of tablet or capsule. This has the advantage of enabling the same mixture of drug and excipients to be used to prepare a range of unit doses of the compound (I) tosylate. Alternatively, if it is desirable to keep the tablet or capsule weight about the same for the different unit dosages, the relative quantities of the Compound (I) tosylate and one or more of the other excipients may be adjusted accordingly. For example in formulations containing microcrystalline cellulose (MCC), the quantity of MCC may be reduced if a higher dose of Compound (I) tosylate is used, thereby maintaining the tablet weight about the same for different formulations.

As will be realised, the formulations of compound (I) tosylate described herein may be used in any of the methods of treatment and medical uses described herein.

In a further embodiment of the invention the crystalline compound (I) 2,5-dimethylbenzenesulfonate described herein (for example Form A thereof) may also be suitable in the pharmaceutical composition, methods of treatment and medical uses described herein.

In a further aspect of the invention we provide a novel process for the synthesis of compound (I) tosylate. In particular, a novel process for the synthesis of compound (I) tosylate Form A is disclosed.

A particular process for the synthesis of compound (I) tosylate is shown in Scheme 2.

Scheme 2

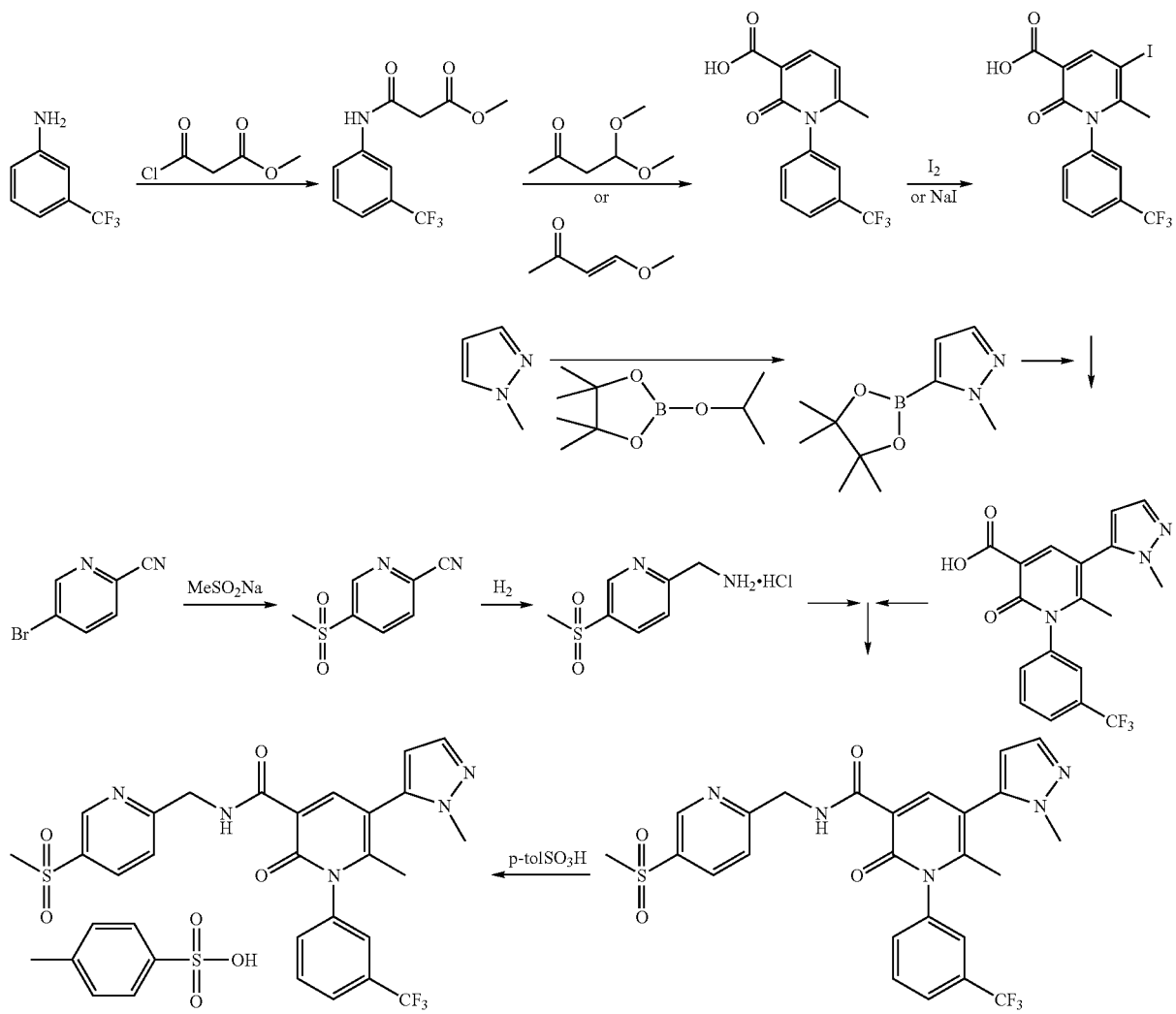

Liquid preparations for oral application may be in the form of syrups or suspensions, for example, solutions containing the compound, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The route outlined in Scheme 2 for the synthesis of compound (I) possesses significant advantages compared to the route disclosed in WO2005/026123.

Thus, the route shown in Scheme 2 involves significantly fewer steps and affords significantly improved yields. The route also minimises the use of potentially toxic reagents such as ethyl iodide and organotin compounds. The route also provides compound (I) in improved purity.

According to a further independent aspect of the invention there is provided a process for the preparation of a compound of the formula (II) or a salt thereof:

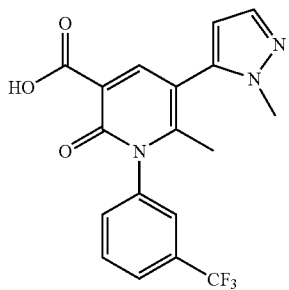

(II)

which process comprises:
coupling, in the presence of a suitable palladium catalyst a base and water, a compound of the formula (III) or a salt thereof:

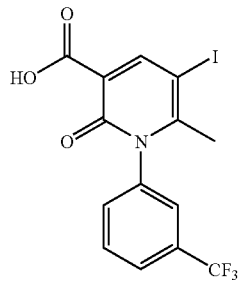

(III)

with a compound of the formula (IV):

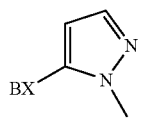

(IV)

wherein BX is a boronic acid or an ester thereof or a trifluoroborate group;
and thereafter, if necessary in any order, removing any protecting groups that are present, converting the compound of formula (II) to a salt or converting a salt of formula (II) back to the free acid form of compound (II).

The group BX in the compound of formula IV is a boronic acid group (B(OH)$_2$) or an ester thereof, or a trifluoroborate group. When BX is a trifluoroborate group it is a suitable salt, for example potassium trifluoroborate. Examples of esters include the pinocol ester. Accordingly a particular compound of the formula (IV) is the compound of the formula (IVa):

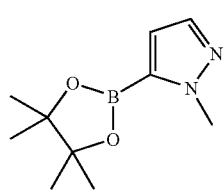

IVa

The coupling reaction is performed in the presence of a suitable base, for example an inorganic or organic base. Suitable inorganic bases include for example, a carbonate such as potassium carbonate or a phosphate such as potassium phosphate dibasic (K$_2$HPO$_3$) or potassium phosphate tribasic (K$_2$PO$_4$). Suitable organic bases include an organic amine such as triethylamine or N-diisopropylethylamine (Hunigs base).

The reaction is performed in the presence of a suitable palladium catalyst. Suitable catalysts include palladium with suitable ligands, typically organo-phosphorus ligands. Conveniently the palladium catalyst is generated in-situ in the reaction mixture by reacting a suitable palladium source, such as palladium (II) acetate or tris(dibenzylideneacetone)dipalladium(0) with the required ligand. Examples of ligands that may be used to generate the catalyst include a ligand selected from 2-dicyclohexylphosphino-2',6'-dimethoxy-1,1'-biphenyl; tri-tert-butylphosphine, triphenylphosphine; tri-(4-fluorophenyl)phosphine; tri-(2-furyl)phosphine; 1-phenyl-2,2,6,6-tetramethylphosphacyclohexan-4-one; phenyldi(tert-butyl)phosphine; tert-butylphenylphosphine; 4,5-bis (diphenylphosphino)-9,9-dimethylxanthene; 4,6-bis (diphenylphosphino)phenoxazine and 1,3,5,7-tetramethyl-6-phenyl-2,4,8-trioxa-6-phosphaadamantane. A particular example of a palladium catalyst include, a catalyst generated by the reaction of palladium (II) acetate and 2-dicyclohexylphosphino-2',6'-dimethoxy-1,1'-biphenyl. A further particular example of a palladium catalyst is (1,1'-(di-tert-butylphosphino)ferrocene)palladium(II) dichloride The reaction is carried out in the presence of water. In addition to the water the reaction is conveniently performed in a suitable solvent, for example acetonitrile, tetrahydrofuran (THF) or methyl ethyl ketone. In one embodiment the reaction is carried out in water and acetonitrile. In another embodiment the reaction is carried out in water, acetonitrile and THF. In another embodiment the reaction is carried out in water and methyl ethyl ketone. The reaction is suitably performed at elevated temperature, for example at the reflux temperature of the solvent system.

The compounds of formulae (III) and (IV) may be prepared, for example, using the methods described in the Examples herein.

According to a further aspect of the present invention there is provided a process for the preparation of compound (I) comprising:
(i) coupling a compound of the formula (III) or a salt thereof with a compound of the formula (IV) as hereinbefore described to form a compound of the formula (II) or a salt thereof; and
(ii) reaction of the compound of formula (II) or salt thereof as hereinbefore defined with a compound of the formula (V) or a salt thereof:

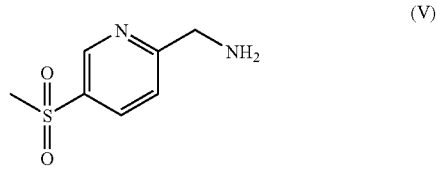

(V)

The reaction in step ii) is carried out under conditions suitable for the formation of an amide from an acid and amine. Suitable reaction conditions include those described in WO 2005/026123, wherein the reaction is performed in the presence of a suitable base and/or coupling agent such as HATU, HOAT, HOBT or DIEA. In a particular embodiment the reaction is performed in the presence of a carbodiimide such as 1,1'-carbonyldiimidazole. In this embodiment the reaction is suitably performed in the presence of a solvent such as acetonitrile, as illustrated in the Examples herein. Compound (V) is suitably used in the form of an acid addition salt, for example the hydrochloride salt. The reaction may also be carried out using an reactive derivative of the compound of formula (II), for example an alkyl ester (such as the methyl or ethyl ester) or an acyl halide, such as the acyl chloride of the compound of formula (II).

Compounds of the formula (V) may be prepared as described in WO 2005/026123, or the Examples herein.

Following the reaction compound (I) tosylate Form A may be prepared using any of the methods described herein.

Accordingly, as a further aspect of the invention there is provided a process for the preparation of compound (I) tosylate From A comprising:

i) reaction of the compound of formula (II) or salt thereof as hereinbefore defined with a compound of the formula (V) or a salt thereof as hereinbefore defined to form compound (I); and ii) converting compound (I) to compound (I) tosylate Form A using any of the processes described hereinbefore for the preparation of compound (I) tosylate Form A.

Accordingly, as a further aspect of the invention there is provided a process for the preparation of compound (I) tosylate From A comprising:

i) coupling a compound of the formula (III) or a salt thereof with a compound of the formula (IV) to form a compound of the formula (II) or a salt thereof as hereinbefore described;

ii) reaction of the compound of formula (II) or salt thereof with a compound of the formula (V) or a salt thereof to form compound (I) as hereinbefore defined; and iii) converting compound (I) to compound (I) tosylate Form A using any of the processes described hereinbefore for the preparation of compound (I) tosylate Form A.

EXAMPLES

The identification of polymorphic forms their crystallinity and solubility were investigated using the following instruments and methods:

Solubility

Solubility was determined in 0.1 M HCl at pH 1.0, 0.2 M phosphate buffer at pH 3, 0.2 M phosphate buffer at pH 5.0, 0.2 M phosphate buffer at pH 6.5 and 0.2 M phosphate buffer at pH 8.

Typically about 4 mg of test sample was added to a 1 ml Scantec glass tube. The experiment was started on addition of 800 µl of preheated test media using an automated Tecon robot system (Genesis Freedom 150). Incubation was at 37° C., in a thermoblock, shaken at 600 rpm. Samples were withdrawn after 1 hour, 3 hours and 24 h, triplicate samples for each media. The supernatant liquid was withdrawn from samples and filtered using a Whatman GF/B filter and diluted prior to analysis by LC (Agilent 1100 series with X Terra MSC18 column). The remaining solid in the sample tubes was characterised using XRPD.

X-Ray Powder Diffraction (XPRD)

XRPD measurements were normally made using a Panalytical X'Pert PRO MPD instrument with the following parameters:

CuK$_\alpha$ (1.5418 Å)
45 kV and 40 mA
$2° \leq 2\theta \leq 40°$
4°/min, incr. 0.016°
Rotating Silicon wafer
Ambient conditions Approximately 2 mg of a test sample was placed on the sample holder and smeared out on the silicon surface using a flat Teflon bar.

Calorimetry (DSC)

The calorimetric response of a test sample to increasing temperature was investigated using a Q1000 Modulated Temperature Differential Scanning Calorimeter (MTDSC) (TA Instruments) using different methods, the main features being:

Normally modulated mode ("heat only") with a ramp rate of 5° C./min (but also 1 and 20° C./min were used without modulation). The temperature range was from just below ambient to close to 300° C.

Approximately 2 mg of the test sample was placed in an aluminium cup with a lid (no crimping).

Gravimetric Analysis (TGA)

The gravimetric response of test samples to increasing temperatures was investigated using a Q500 Thermal Gravimetric Analyser (TGA) (TA Instruments) using the following parameters:

Heating rate (normally): 5° C./min

Approximately 2 to 5 mg of the test sample was placed in the cup and heated to close to 300° C.

Humidity Interaction

The gravimetric responses of test samples to changes in humidity were investigated using a SGA 100 (VTI Corporation) Gravimetrical Vapour Sorption (GVS) instrument with the following features:

Dry to 90% RH and back, in steps of, for example, 10% RH.
Equilibrium condition: <0.01 weight-% per 10 minutes (<0.001 weight-%/min)

Approximately 5 mg of the test sample was placed in the cup and evaluated.

Morphology

The morphology of a typical test sample was investigated using a Jeol JSM-5200 Scanning Electron Microscope (SEM) using a magnification of up to 3500 times. A few particles were sprinkled onto the sample holder with a carbon sticky tape and coated with a thin gold layer and investigated.

General Chemical Methods $^1$H NMR and $^{13}$C NMR spectra were recorded on a 300 MHz Varian Unity Inova or 400 MHz Varian Unity Inova instrument. The central peaks of chloroform-d ($\delta_H$ 7.27 ppm), dimethylsulfoxide-d$_6$ ($\delta_H$ 2.50 ppm), acetonitrile-d$_3$ ($\delta_H$ 1.95 ppm) or methanol-d$_4$ ($\delta_H$ 3.31 ppm) were used as internal references. Column chromatography was carried out using silica gel (0.040-0.063 mm, Merck). Starting materials were commercially available unless otherwise stated. All solvents and commercial reagents were of laboratory grade and were used as received. Unless otherwise stated, operations were conducted at ambient temperature, typically 20 to 25° C.

LC analysis was performed using Agilent 1100 HPLC instruments. Various LC methods were used for product analysis.

LCMS analysis was performed using WATERS 2790 HPLC with 996 Photo Diode Array Detector and MicroMass ZMD, Single Quadrupole Mass Spectrometer with Z-spray interface.

ABBREVIATIONS eq equivalent
rel relative
vol volume
vol eq volume of material required relative to the limiting reagent
DMSO dimethyl sulfoxide
mol eq molar equivalent of material relative to the limiting reagent
THF tetrahydrofuran

Example 1

Methyl 3-oxo-3-(3-(trifluoromethyl)phenylamino)propanoate

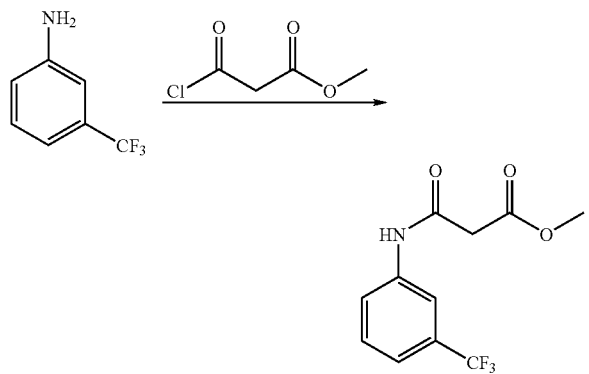

Sodium hydrogen carbonate (26.0 kg, 1.7 mol eq) was charged followed by acetone (58.6 L, 2 rel vol). 3-(Trifluoromethyl)aniline (29.3 kg, 1 mol eq, limiting reagent) was charged followed by addition of acetone (14.7 L, 0.5 rel vol) and the mixture cooled to 0° C. Methyl malonyl chloride (25.8 kg, 1.05 mol eq) was diluted with acetone (29.3 L, 1 rel vol) and charged maintaining the temperature below 20° C. An acetone line rinse (14.7 L, 0.5 rel vol) was charged and the reaction mixture was stirred until HPLC confirmed the reaction to be complete. Water (293 L, 10 rel vol) was then charged and acetone was removed by distillation. The reaction was then cooled to 20° C. A further portion of water was added (171.2 L, 4 rel vol) and the reaction was stirred to precipitate out the product. The solid was isolated by filtration, washed twice with water (2×58.6 L, 2×2 rel vol), once with iso-hexane (146.5 L, 5 rel vol) and dried to constant weight to yield the title compound (39.5 kg, 151.7 mol, 84%); $^1$H NMR (CDCl$_3$): δ 3.51 (s, 2H); 3.82 (s, 3H); 7.38 (d, 1H, J=7.9 Hz); 7.45 (t, 1H, J=7.9 Hz); 7.76 (d, 1H, J=7.7 Hz); 7.85 (s, 1H); 9.42 (s, 1H) ppm; LCMS: m/z 262.2 (MH$^+$).

Example 1a

Alternative Preparation of methyl 3-oxo-3-(3-(trifluoromethyl)phenylamino)propanoate Sodium hydrogen carbonate (36.3 kg, 1.7 mol eq) was charged followed by iso-propylacetate (102.5 L, 2.5 rel vol). 3-(trifluoromethyl)aniline (41.0 kg, 1 mol eq, limiting reagent) charged followed by a line rinse of iso-propylacetate (20.5 L, 0.5 rel vol). The reaction was cooled to 5° C.-10° C. Methyl malonyl chloride (36.5 kg, 1.05 mol eq) was charged maintaining the temperature below 10° C. followed by a line rinse of iso-propylacetate (10.3 L, 0.25 rel vol). The mixture was stirred until the reaction was complete as judged by HPLC. The temperature was adjusted to 20° C. and further iso-propylacetate (71.8 L, 1.75 rel vol) charged followed by water (205 L, 5 rel vol). The layers were separated & the organic layer further extracted with brine (41 L, 1 rel vol). The solvent was swapped from iso-propylacetate to cyclohexane by reduced pressure distillation. Following seeding, cooling to 5° C. and stirring, the product was isolated by filtration, washed twice with cyclohexane (2×41 L, 2×1 rel vol) and dried to constant weight to yield the title compound (60.6 kg, 232.2 mol, 91%).

Example 2

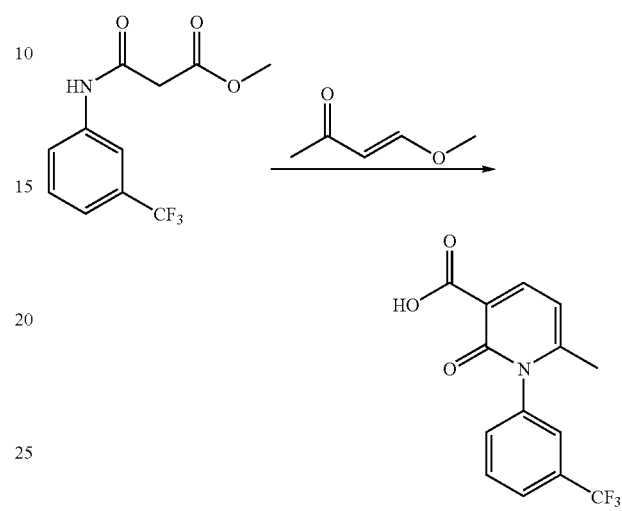

6-Methyl-2-oxo-1-[3-(trifluoromethyl)phenyl]-1,2-dihydropyridine-3-carboxylic acid Methyl 3-oxo-3-(3-(trifluoromethyl)phenylamino)propanoate (39.5 kg, 1 mol eq, limiting reagent) was dissolved in ethanol (197.5 L, 5.0 rel vol). Sodium methoxide solution in methanol (74.6 kg, 25% w/w, 2.3 mol eq) was charged followed by an ethanol line wash (11.9 L, 0.3 rel vol). trans-4-Methoxy-3-buten-2-one (19.2 kg, 1.2 mol eq) in ethanol (26.5 L, 0.67 rel vol) was charged. The reaction was heated to 65° C. and stirred at this temperature until the reaction was deemed complete as judged by HPLC analysis. Water (67.2 L, 1.7 rel vol) and 2 M aqueous sodium hydroxide (29.6 L, 0.75 rel vol) were then added and the reaction mixture was stirred for 1 hour. To the solution was added 8 M aqueous hydrochloric acid (237.0 L, 6 rel vol) and the mixture stirred for a further 1 hour. The solution was cooled, stirred and isolated by filtration. The solid was washed with water (79.2 L, 2 rel vol) and iso-hexane (59.2 L, 1.5 rel vol) and dried to constant weight to yield the title compound (28.6 kg, 96.2 mol, 63% (uncorrected for assay)); $^1$H NMR (CDCl$_3$): δ 2.14 (s, 3H); 6.57 (d, 1H, J=7.4 Hz); 7.46 (d, 1H, J=8.2 Hz); 7.52 (s, 1H); 7.77 (t, 1H, J=7.8 Hz); 7.85 (d, 1H, J=7.9 Hz); 8.53 (d, 1H, J 7.4 Hz); 13.66 (s, 1H) ppm; LCMS: m/z 298.3 (MH$^+$).

Example 2a

Alternative Preparation of 6-methyl-2-oxo-1-[3-(trifluoromethyl)phenyl]-1,2-dihydropyridine-3-carboxylic acid Methyl 3-oxo-3-(3-(trifluoromethyl)phenylamino)propanoate (62.0 kg, 1 mol eq, limiting reagent) was charged followed by ethanol (310 L, 5 rel vol, 5.3 rel vol). 4,4-dimethoxybutan-2-one (37.6 kg, 1.2 mol eq) was charged followed by an ethanol line rinse (18.6 L, 0.3 rel vol) and the temperature adjusted to 50° C. Sodium methoxide (30% w/w in methanol) (141.0 kg, 3.3 mol eq) charged maintaining the temperature below 55° C. An ethanol line rinse (31.0 L, 0.5 rel vol) was applied. The reaction was stirred until complete as judged by HPLC. Water (105.4 L, 1.7 rel vol) and 29% aqueous sodium hydroxide solution (17.2 kg, 0.52 mol eq) were charged. The reaction was stirred for 60 minutes. Hydrochloric acid (30% w/w) was charged until pH 2 achieved and was then cooled. The product was isolated by filtration, washed five times with water (5×124 L, 5×2 rel vol) and dried under vacuum to constant weight yielding the title compound (50.9 kg, 171.4 mol, 73.5%).

Example 3

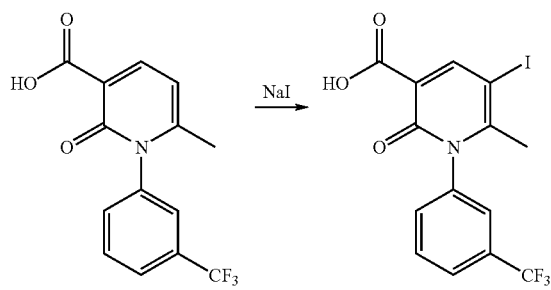

5-Iodo-6-methyl-2-oxo-1-[3-(trifluoromethyl)phenyl]-1,2-dihydropyridine-3-carboxylic acid To 6-methyl-2-oxo-1-[3-(trifluoromethyl)phenyl]-1,2-dihydropyridine-3-carboxylic acid (28.6 kg, 1 mol eq, limiting reagent) was added sodium iodide (15.1 kg, 1.05 mol eq) and acetic acid (200.2 L, 7 rel vol). 90% Nitric acid (20.1 kg, 3.0 mol eq) was added dropwise. The reaction was heated to 50° C. and stirred until an HPLC assay showed reaction to be complete. The reaction was cooled and stirred. The precipitated product was collected by filtration, washed with water (171.6 L, 6 rel vol) and dried to constant weight to yield the title compound (19.2 kg, 45.4 mol, 68%); $^1$H NMR (CDCl$_3$): δ 2.36 (s, 3H); 7.42 (d, 1H, J=8.1 Hz); 7.50 (s, 1H); 7.78 (t, 1H, J=7.8 Hz); 7.85 (d, 1H, J=7.9 Hz); 8.86 (s, 1H); 13.44 (s, 1H) ppm; LCMS: m/z 424.0 (MH$^+$).

Example 3A

Alternative Preparation of 5-iodo-6-methyl-2-oxo-1-[3-(trifluoromethyl)phenyl]-1,2-dihydropyridine-3-carboxylic acid To acetic acid (263.7 L, 6.8 rel vol) was charged 6-methyl-2-oxo-1-[3-(trifluoromethyl)phenyl]-1,2-dihydropyridine-3-carboxylic acid (38.6 kg, 1 mol eq, limiting reagent), iodine (17.4 kg, 0.53 mol eq) and concentrated sulfuric acid (3.7 L, 0.1 rel vol). The temperature was adjusted to 50° C.-55° C. and 90% nitric acid (4.1 kg, 0.6 mol eq) charged over 15 minutes. The reaction was stirred until deemed to be complete as judged by HPLC analysis. The reaction was cooled, stirred and the product collected by filtration. The solid was washed twice with water (2×77.0 L, 2×2 rel vol) and acetone (2×38.6 kg, 2×1 rel vol). The solid was dried under vacuum to constant weight to yield the title compound (47.0 kg, 111.0 mol, 85.7%).

Example 4

1-Methyl-5-(4,4,5,5-tetramethyl-1,3,2-dioxaborolan-2-yl)-1H-pyrazole

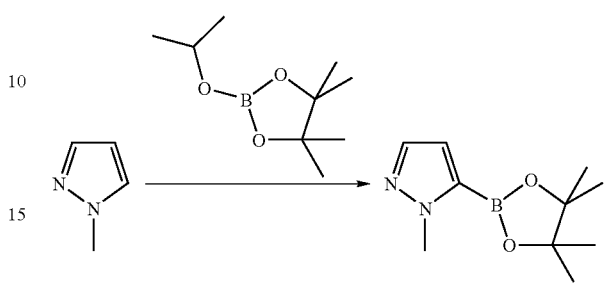

N-Methylpyrazole (6.0 kg, 1 mol eq, limiting reagent) was charged, followed by anhydrous tetrahydrofuran (84 L, 14 rel vol) and the reaction mixture was cooled to −10° C. n-Hexyllithium (2.3 M solution in hexanes, 23.6 kg, 1.05 mol eq) was charged keeping the temperature below −5° C., followed by a line rinse of iso-hexane (1.2 L, 0.2 rel vol). The reaction mixture was stirred at below −5° C. 2-Isopropoxy-4,4,5,5-tetramethyl-1,3,2-dioxaborolane (14.9 kg, 1.1 mol eq) was diluted with anhydrous tetrahydrofuran (6.0 L, 1 rel vol) and was charged to the reaction keeping the temperature below 0° C. A line rinse with anhydrous tetrahydrofuran (3.0 L, 0.5 rel vol) was charged and the reaction mixture was stirred for around 30 minutes. The reaction was warmed to 25° C. A solution of glacial acetic acid (6.6 kg, 1.5 mol eq) in water (36 L, 6 rel vol) was charged to the reaction over about 30 minutes. The reaction mixture was stirred for around 30 minutes. The phases were separated and the organic layer retained. Change of solvent to acetonitrile by distillation afforded the title compound as a solution in acetonitrile. The solution yield of the title compound was determined by GC assay; $^1$H NMR (d$_6$-DMSO): δ 1.31 (s, 12H), 3.98 (s, 3H), 6.62 (d, 1H, J=1.9 Hz), 7.45 (d, 1H, J=2.1 Hz) ppm.

Note: if (1,1'-(di-tert-butylphosphino)ferrocene)palladium (II) dichloride is used as catalyst in Example 5 then the solvent change to acetonitrile in the last step of this process is not required.

Example 5

6-Methyl-5-(1-methyl-1H-pyrazol-5-yl)-2-oxo-1-[3-(trifluoromethyl)phenyl]-1,2-dihydropyridine-3-carboxylic acid

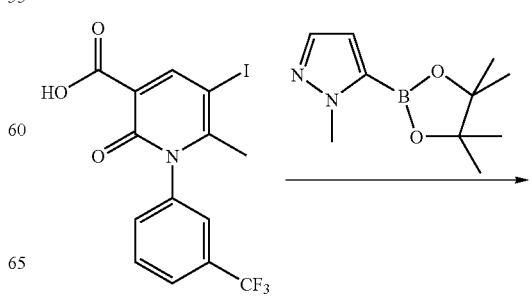

-continued

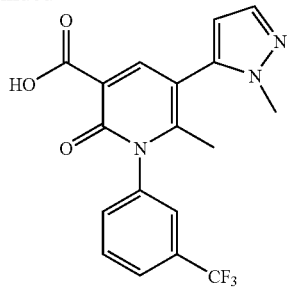

Acetonitrile (30.3 L, 3 rel vol) was charged, followed by palladium(II) acetate (260 g, 0.05 mol eq) and 2-dicyclohexylphosphino-2',6'-dimethoxy-1,1'-biphenyl (980 g, 0.1 mol eq). The mixture was stirred for 15 minutes. A solution of potassium carbonate (10.0 kg, 3.0 mol eq) in water (60.6 L, 6 rel vol) was added to the reaction. 1-Methyl-5-(4,4,5,5-tetramethyl-1,3,2-dioxaborolan-2-yl)-1H-pyrazole (31.8% w/w, 20.3 kg, 1.3 mol eq) as a solution in acetonitrile was added, followed by 5-iodo-6-methyl-2-oxo-1-[3-(trifluoromethyl)phenyl]-1,2-dihydropyridine-3-carboxylic acid (10.1 kg, 1 mol eq, limiting reagent). The reaction mixture was heated to reflux and stirred until the reaction was complete as judged by HPLC analysis. The reaction mixture was cooled and filtered. The cake was washed with acetonitrile (10.1 L, 1 rel vol) and the cake discarded. The filtrate was heated to 50° C. 6 M Hydrochloric acid (60.6 L, 6 rel vol) was added carefully to the reaction. The reaction mixture was stirred at 50° C. for 60 minutes, cooled to 5° C. and stirred overnight. The solid was collected by filtration, washed twice with water (2×20.2 L, 2×2 rel vol) and with cold (around 5° C.) acetonitrile (10.1 L, 1 rel vol). The solid was dried to constant weight to yield the title compound (8.1 kg, 21.5 mol, 77%); $^1$H NMR ($d_6$-DMSO): δ 1.87 (s, 3H); 3.73 (s, 3H); 6.35-6.37 (m, 1H); 7.54-7.55 (m, 1H); 7.83-7.91 (m, 2H); 7.95-7.97 (m, 1H); 8.07 (s, 1H); 8.25 (s, 1H); 13.80 (s, 1H); LCMS: m/z 378.3 (MH$^+$).

Example 5a

Alternative Preparation of 6-methyl-5-(1-methyl-1H-pyrazol-5-yl)-2-oxo-1-[3-(trifluoromethyl)phenyl]-1,2-dihydropyridine-3-carboxylic acid To 1-methyl-5-(4,4,5,5-tetramethyl-1,3,2-dioxaborolan-2-yl)-1H-pyrazole (322.0 kg, 12.2% w/w as a solution in THF/hexanes, 1.7 mol eq) was charged acetonitrile (117.5 L, 2.5 rel vol). (1,1'-(di-tert-butylphosphino)ferrocene)palladium(II) dichloride (3.79 kg, 0.05 mol eq) was charged followed by water (235 L, 5 rel vol). Following stirring triethylamine (33.7 kg, 3 mol eq) was charged and a water line rinse applied (47.0 L, 1 rel vol). Following further stirring 5-iodo-6-methyl-2-oxo-1-[3-(trifluoromethyl)phenyl]-1,2-dihydropyridine-3-carboxylic acid (47.0 kg, 1 mol eq, limiting reagent) was charged. The reaction was heated and stirred until reaction judged to be complete by HPLC analysis. The reaction was cooled and N-acetyl-L-cysteine (1.9 kg, 0.1 mol eq) charged. Following further stirring, the reaction was filtered. The filtrate was heated and 4 M sulfuric acid (118.7 L, 2.5 rel vol) charged. The reaction was stirred and then cooled. The product was isolated by filtration. The solid was washed twice with water (2×94 L, 2×2 rel vol) and acetonitrile (47.0 L, 1 rel vol) and dried to constant weight yielding the title compound (35.0 kg, 92.8 mol, 83%).

Example 6

6-Methyl-5-(1-methyl-1H-pyrazol-5-yl)-N-((5-(methylsulfonyl)pyridin-2-yl)methyl)-2-oxo-1-[3-(trifluoromethyl)phenyl]-1,2-dihydropyridine-3-carboxamide (compound (I))

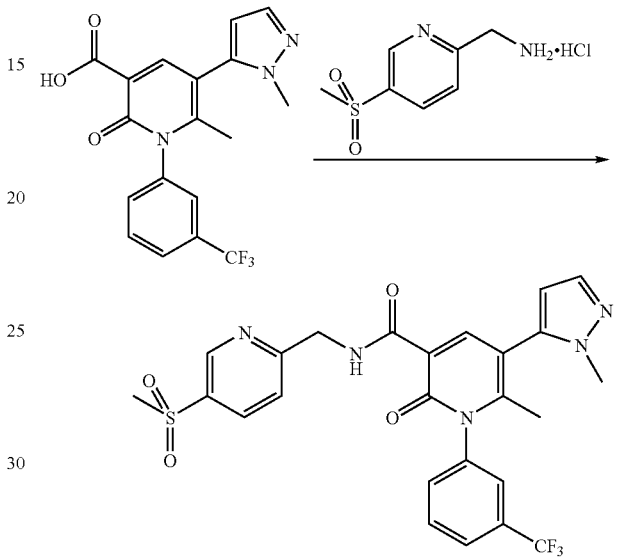

6-Methyl-5-(1-methyl-1H-pyrazol-5-yl)-2-oxo-1-[3-(trifluoromethyl)phenyl]-1,2-dihydropyridine-3-carboxylic acid (52.0 kg, 1 mol eq, limiting reagent) and acetonitrile (208 L, 4 rel vol,) were charged. The reaction mixture was heated to 50° C. 1,1'-s carbonyldiimidazole as a solution in acetonitrile (208 L, 4 rel vol) is charged to the reaction until the reaction is complete as judged by HPLC. C-(5-(Methanesulfonyl)pyridine-2-yl)methylamine monohydrochloride (33.8 kg, 1.1 mol eq) was charged and the reaction maintained at 50° C. until the reaction was deemed complete as judged by HPLC. Water (780 L, 15 rel vol) was charged. The reaction mixture was stirred, cooled and further stirred. The solid was collected by filtration and washed twice with water (2×104 L, 2×2 rel vol) and dried to constant weight to yield the title compound (96.0 kg, 176.0 mol, 96%); $^1$H NMR ($d_6$-DMSO): δ 1.83 (s, 3H); 3.29 (s, 3H); 3.72 (s, 3H); 4.73 (d, 2H, J 5.8 Hz); 6.33 (d, 1H, J=1.9 Hz); 7.53 (d, 1H, J=1.9 Hz); 7.57 (d, 1H, J 8.3 Hz); 7.81-7.88 (m, 2H); 7.92-7.94 (m, 1H); 8.03 (s, 1H); 8.21 (s, 1H); 8.27 (dd, 1H, J 2.3, 7.9 Hz); 8.99 (d, 1H, J=2.3 Hz); 10.06 (t, 1H, J 6.0 Hz); LCMS: m/z 546.3 (MH$^+$).

Intermediate

The C-(5-methanesulfonyl-pyridin-2-yl)-methylamine hydrochloride used as the starting material was prepared as follows.

5-Methanesulfonyl-pyridine-2-carbonitrile

To 5-Bromo-2-cyanopyridine (17.5 kg, 1 mol eq, limiting reagent) and DMSO (103.6 L, 6 rel vol) was charged sodium methanesulfinate (13.7 kg, 1.4 mol eq) and the reaction heated to 100° C. for 24 hours. The reaction mixture was cooled to 50° C. and the product precipitated by addition of water (163 L, 9.3 rel vol). The mixture was then cooled to 25° C. and stirred for at least 9 hours. The solid was collected by filtration, washed twice with water (40 L, 2.3 rel vol) and dried to constant weight yielding the title compound (10.9 kg, 5.9 mol, 60%; $^1$H NMR (CDCl$_3$): 9.24 (dd, 1H, J 0.8, 2.3 Hz); 8.41 (dd, 1H, J 2.3, 8.2 Hz); 7.93 (dd, 1H, J 0.8, 8.2 Hz); 3.17 (s, 3H) ppm.

Alternative preparation of 5-methanesulfonyl-pyridine-2-carbonitrile

5-Bromo-2-cyanopyridine (38.0 kg 1.0 mol eq, limiting reagent) and sodium methane sulfinate (29.68 kg, 1.4 mol eq) were charged followed by DMSO (228 L, 6 rel vol). The reaction was heated to 100° C.-105° C. and stirred until reaction complete as judged by HPLC analysis. After cooling, the reaction mixture was added to preheated water (356 L, 9.4 rel vol). After cooling and stirring, the product was isolated by filtration. The solid was washed with water (456 L, 12 rel vol) and dried to constant weight to yield the title compound (33 kg, 18.1 mol, 87%).

C-(5-Methanesulfonyl-pyridin-2-yl)-methylamine monohydrochloride

To 5-methanesulfonyl-pyridine-2-carbonitrile (3.0 kg, 1 mol eq, limiting reagent) was charged absolute ethanol (30.7 L, 10 rel vol), 32% aqueous 6 M hydrochloride acid (3.9 kg, 2 mol eq) and palladium on carbon (303 g, 1.50 g, 10% w/w). The reaction was stirred under a hydrogen atmosphere (2.5 bar) at 25° C. until the reaction was complete as judged by HPLC analysis. Water (5.4 L, 1.8 rel vol) was charged. The mixture was filtered through Celite and washed with water (1.8 L, 0.6 rel vol). The reaction mixture was concentrated under reduced pressure and ethanol (30.0 L, 10 rel vol) charged. The mixture was cooled, stirred and the product collected by filtration. The solid was washed with ethanol (16.9 L, 5.6 rel vol) and the solid dried to constant weight yielding the title compound (3.1 kg, 13.8 mol, 84%); $^1$H NMR (d$_6$-DMSO): 9.10 (d, 1H, J=2.4 Hz), 8.73 (br s, 3H), 8.41 (dd, 1H, J 2.4, 8.3 Hz), 7.82 (d, 1H, J=8.2 Hz), 4.30-4.34 (m, 2H), 3.35 (s, 3H) ppm; LCMS: m/z 187.3 (MH$^+$).

Alternative preparation of C-(5-methanesulfonyl-pyridin-2-yl)-methylamine monohydrochloride To 5-Methanesulfonyl-pyridine-2-carbonitrile (22 kg, 1.0 mol eq, limiting reagent) was charged palladium on carbon (2.0 kg, 5% w/w), ethanol (110 L, 5 rel vol), water (14 L, 0.64 rel vol) and hydrochloric acid (25.04 kg, 32% w/w). An ethanol line rinse (16 L, 0.7 rel vol) followed. The reaction mixture was heated and subjected to an atmosphere of hydrogen until the reaction was complete as judged by HPLC analysis. Water (108 L, 4.9 rel vol) was charged, the catalyst filtered off and washed with water (36 L, 1.6 rel vol). The combined filtrates were concentrated under reduced pressure to approximately 2.5 rel vols. The reaction was then heated and ethanol (126.3 L, 5.7 rel vol) was charged. The reaction mixture was cooled, stirred and isolated by filtration. The solid was washed with ethanol (73.7 L, 3.3 rel vol) and dried to constant weight to yield the title compound (20.1 kg, 9.05 mol, 82%).

Example 7

6-Methyl-5-(1-methyl-1H-pyrazol-5-yl)-N-((5-(methylsulfonyl)pyridin-2-yl)methyl)-2-oxo-1-[3-(trifluoromethyl)phenyl]-1,2-dihydropyridine-3-carboxamide tosylate Form A (compound (I) tosylate form A)

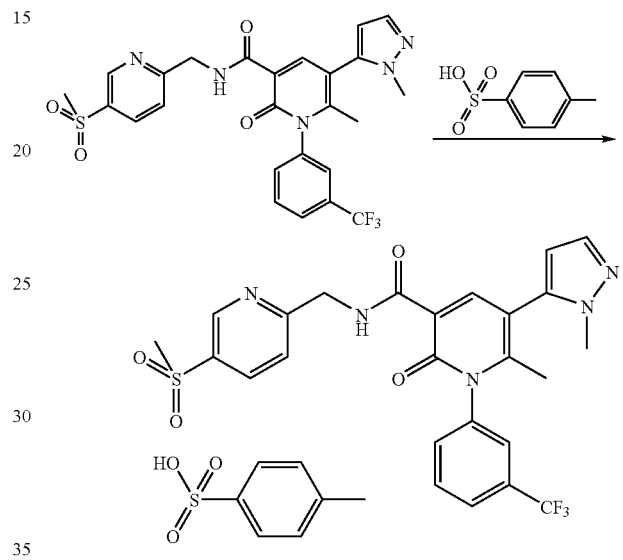

6-Methyl-5-(1-methyl-1H-pyrazol-5-yl)-N-((5-(methylsulfonyl)pyridin-2-yl)methyl)-2-oxo-1-[3-(trifluoromethyl)phenyl]-1,2-dihydropyridine-3-carboxamide (6.06 g, 1.0 mol eq, limiting reagent) and acetonitrile (121.7 mL, 20 rel vol) were charged and heated to 80° C. A solution of 4-toluenesulfonic acid monohydrate (2.11 g, 1.0 mol eq) in acetonitrile (24.34 mL, 4 rel vol) was added. Temperature cycling between 80° C. and 5° C. was performed (optional step). Upon reaching 5° C., the slurry was passed through an in-line rotor-stator mill and the solid was collected by filtration, washed twice with acetonitrile (9.13 mL, 1.5 rel vol) and dried to constant weight yielding the title compound (5.98 g, 8.34 mmol, 76%); $^1$H NMR (d$_6$-DMSO): δ 1.83 (s, 3H); 2.29 (s, 3H); 3.29 (s, 3H); 3.72 (s, 3H); 4.73 (d, 2H, J=5.6 Hz); 6.34 (d, 1H, J=1.8 Hz); 7.12 (d, 2H, J=7.7 Hz); 7.46-7.49 (m, 2H); 7.54-7.55 (m, 1H); 7.58 (d, 1H, J=8.5 Hz); 7.82-7.88 (m, 2H); 7.92-7.94 (m, 1H); 8.03 (s, 1H); 8.22 (s, 1H); 8.28 (dd, 1H, J 2.3, 8.2 Hz); 8.99-9.0 (m, 1H); 10.07 (t, 1H, J 5.7 Hz) ppm; LCMS: m/z 546.3 [MH-tosylate].

Example 7a

Large Scale Preparation of Compound (I) Tosylate Form A

6-Methyl-5-(1-methyl-1H-pyrazol-5-yl)-N-((5-(methylsulfonyl)pyridin-2-yl)methyl)-2-oxo-1-(3-trifluoromethyl)phenyl]-1,2-dihydropyridine-3-carboxamide (45.3 kg, 83.0 mol, limiting reagent) and acetonitrile (906 L, 20 rel vol) were charged to a reaction vessel and heated to 80° C. A solution of 4-toluenesulfonic acid monohydrate (15.9 kg, 1.0 mol eq) in acetonitrile (181.2 L, 4 rel vol) was added. Following an acetonitrile line rinse (45.3 L, 1 rel vol), temperature cycling between 80° C. and 5° C. was performed. Upon reaching 5° C., the solid was collected by filtration, washed twice with acetonitrile (68.0 L, 1.5 rel vol) and dried to constant weight yielding the title compound (52.8 kg, 73.6 mol, 89%).

If required, the compound (I) tosylate Form A could be milled prior to isolation by filtration using a similar method to that disclosed in Example 7a above.

Example 8

Preparation of salts of 6-methyl-5-(2-methyl-2H-pyrazol-3-yl)-2-oxo-1-(3-trifluoromethylphenyl)-1,2-dihydro-pyridine-3-carboxylic acid (5-methanesulfonylpyridin-2-ylmethyl)-amide Example 8a Compound (I) Tosylate Form A 6-Methyl-5-(2-methyl-2H-pyrazol-3-yl)-2-oxo-1-(3-trifluoromethylphenyl)-1,2-dihydropyridine-3-carboxylic acid (5-methanesulfonylpyridin-2-ylmethyl)-amide (compound (I)) (4.50 g, 8.26 mmol) was dissolved in acetonitrile (270 ml). Toluene-4-sulfonic acid (1.57 g, 8.26 mmol) dissolved in acetonitrile (13 ml) was added at room temperature to the stirred solution of compound (I). The product soon starts to precipitate. The suspension was stirred over night. Approximately 100 ml of the acetonitrile was removed by evaporation. The suspension was stirred again over night and was then filtered. The product was dried under vacuum at 50° C. to give the title product; yield 5.18 g, 7.22 mmol, 87%

Example 8b

Compound (I) mesylate

Compound (I) mesylate was synthesised using an analogous method to that described for the synthesis of compound (I) tosylate in Example 8a from compound (I) (2.0 g, 3.67 mmol) and methane sulfonic acid (0.35 g, 3.67 mmol) to give the title product; yield 2.2 g, 3.45 mmol, 94%.

Example 8c

Compound (I) p-xylene-2-sulfonate (2,5-dimethylbenzenesulfonate) Form A

Compound (I) p-xylene-2-sulfonate was synthesized using an analogous method to that described for the synthesis of compound (I) tosylate in Example 8a from compound (I) (50 mg, 0.092 mmol) and p-xylene-2-sulfonic acid (20 mg, 0.092 mmol). No precipitation was obtained after stirring over night. After the evaporation of 50% of the solvent and stirring for an extra night a good precipitation of the title product was obtained; yield 56 mg, 0.076 mmol, 83%. The compound (I) p-xylene-2-sulfonate (2,5-dimethylbenzenesulfonate) Form A was crystalline and gave the powder X-ray diffraction pattern shown in FIG. 8.

Example 8d

Compound (I) esylate

Compound (I) esylate was synthesized using an analogous method to that described for the synthesis of compound (I) tosylate in Example 8a from compound (I) (50 mg, 0.092 mmol) and ethane sulfonic acid (9.3 mg, 0.092 mmol). No precipitation was obtained after stirring over night. The solvent was evaporated and ethyl acetate (2 ml) was added. A suspension was formed. The suspension was stirred over night, was filtered and dried under vacuum at 50° C. to give the title product; yield 49 mg, 0.075 mmol, 81%

Example 8e

Compound (I) 1,5-naphthalenedisulfonate

An attempt to synthesize compound (I) 1,5-naphtalenedisulfonic acid salt was made using the same procedure used for the preparation of compound (I) tosylate described in Example 8a using compound (I) (50 mg, 0.092 mmol) and 1.0 or 0.5 equivalents of 1,5-naphthalenedisulfonic acid (26.5 mg, 0.092 mmol) or (13.3 mg, 0.046 mmol). Due to the very low solubility of the sulfonic acid extra acetonitrile (200 µl) and methanol (100 µl) were added. In both reactions precipitates were formed. The suspensions were stirred over night. Next day the precipitations had transformed into gum like solids. The crystallizations were stopped and the solvents were evaporated. Three other solvents were tested, as follows.

The residues from the two experiments described above were divided into three parts each. To each part was added a solvent selected from ethanol, dioxane or ethyl acetate. Slurries were formed and were stirred over night. The solids from the slurries were substantially amorphous or poorly crystalline.

Example 8f

Compound (I) hydrochloride

An attempt was made to synthesize compound (I) hydrochloride using the same method described in Example 8a for the preparation of compound (I) tosylate from compound (I) (50 mg, 0.092 mmol) and hydrochloric acid (92 µl, 0.092 mmol, 1M in water). No precipitation was observed after stirring over night. The solvent was evaporated and ethyl acetate (2 ml) was added. A suspension was formed. The suspension was stirred over night. The solid was substantially amorphous or poorly crystalline.

Example 8g

Compound (I) sulfate

An attempt was made to synthesize compound (I) sulfate using the same method described in Example 8a for the preparation of compound (I) tosylate from compound (I) (50 mg, 0.092 mmol) and sulfuric acid (2 g) (92 µl, 0.092 mmol, 1M in water). No precipitation was obtained after stirring over night. The solvent was evaporated and acetonitrile (1 ml) was added. A suspension was formed. The suspension was stirred over night. The solid was substantially amorphous or poorly crystalline.

Example 9

6-Methyl-5-(1-methyl-1H-pyrazol-5-yl)-N-((5-(methylsulfonyl)pyridin-2-yl)methyl)-2-oxo-1-[3-(trifluoromethyl)phenyl]-1,2-dihydropyridine-3-carboxamide tosylate (compound (I) tosylate Form A) prepared from solvents other than acetonitrile Example 9a To compound (I) (3 g, 1.0 mol eq, limiting reagent) was charged tetrahydrofuran (120 mL, 40 rel vol). The temperature was adjusted to 65° C. and a solution formed. p-Toluenesulfonic acid monohydrate (1.06 g, 1.0 mol eq) was dissolved in tetrahydrofuran (6.0 mL, 2 rel vol). This solution was charged to the reaction. Following stirring and cooling, the solid was isolated by filtration, washed with tetrahydrofuran (6.0 mL, 2 rel vol) and dried to constant weight yielding the compound (I) tosylate (3.52 g, 4.90 mmol, 89%).

Example 9b

To compound (I) (3 g, 1.0 mol eq, limiting reagent) was charged butyronitrile (45 mL, 15 rel vol). The temperature was adjusted to 100° C. and a solution formed. p-Toluenesulfonic acid monohydrate (1.06 g, 1.0 mol eq) was dissolved in butyronitrile (18 mL, 6 rel vol). This solution was charged to the reaction. Following stirring and cooling, the solid was isolated by filtration, washed with butyronitrile (4.5 mL, 1.5 rel vol) and dried to constant weight yielding the compound (I) tosylate (3.37 g, 4.70 mmol, 85%).

Example 9c

To compound (I) (5 g, 1.0 mol eq, limiting reagent) was charged methyl ethyl ketone (150 mL, 30 rel vol). The temperature was adjusted to 80° C. and a solution formed. p-Toluenesulfonic acid monohydrate (1.76 g, 1.0 mol eq) was dissolved in methyl ethyl ketone (20 mL, 5 rel vol). This solution was charged to the reaction. A line rinse of methyl ethyl ketone (5 mL, 1 rel vol) was applied. Following stirring, temperature cycling and cooling, the solid was isolated by filtration, washed twice with methyl ethyl ketone (2×25 mL, 2×5 rel vol) and dried to constant weight yielding the compound (I) tosylate (5.93 g, 8.19 mmol, 89%).

Example 9d

To compound (I) (2.5 g, 1.0 mol eq, limiting reagent) was charged cyclohexanone (50 mL, 20 rel vol). The temperature was adjusted to 80° C. and a solution formed. p-Toluenesulfonic acid monohydrate (881 mg, 1.0 mol eq) was dissolved in cyclohexanone (10 mL, 4 rel vol). This solution was charged to the reaction. A cyclohexanone line rinse (2.5 mL, 1 rel vol) was charged. Following stirring, temperature cycling and cooling, the solid was isolated by filtration, washed twice with cyclohexanone (2×3.75 mL, 2×1.5 rel vol) and dried to constant weight yielding compound (I) tosylate (2.31 g, 3.14 mmol, 69%).

Example 9e

To compound (I) (5 g, 1.0 mol eq, limiting reagent) was charged acetone (150 mL, 30 rel vol). The temperature was adjusted to 55° C. and a solution formed. p-Toluenesulfonic acid monohydrate (1.77 g, 1.0 mol eq) was dissolved in acetone (10 mL, 2 rel vol). This solution was charged to the reaction. Following stirring and cooling, the solid was isolated by filtration, washed with acetone (10 mL, 2 rel vol) and dried to constant weight yielding compound (I) tosylate (5.98 g, 8.33 mmol, 91%).

Example 9f

To compound (I) (3 g, 1.0 mol eq, limiting reagent) was charged butan-1-ol (135 mL, 45 rel vol). The temperature was adjusted to 100° C. and a solution formed. p-Toluenesulfonic acid monohydrate (1.06 g, 1.0 mol eq) was dissolved in butan-1-ol (12 mL, 4 rel vol). This solution was charged to the reaction. A butan-1-ol line rinse (3 mL, 1 rel vol) was charged. Following stirring, temperature cycling and cooling, the solid was isolated by filtration, washed twice with butan-1-ol (2×4.5 mL, 2×1.5 rel vol) and dried to constant weight yielding compound (I) tosylate (2.96 g, 4.03 mmol, 73%).

Characterisation of Compound (I) Tosylate Form A

X-ray powder diffraction of Compound (I) tosylate Form A (FIG. 1) indicates that the material is crystalline. The most prominent peaks from the XRPD pattern of compound (I) tosylate Form A are described hereinbefore and listed in Table 3. Differential Scanning Calorimetry (DSC) on compound (I) tosylate Form A shows a single melting endotherm with an onset at about 237° C. (FIG. 2). No appreciable weight losses are observed by Thermogravimetric analysis (FIG. 2). Humidity sorption measurements using gravimetrical vapour sorption (GVS) showed compound (I) tosylate Form A to have a very low humidity uptake of around 0.2% at 80% RH.

Bioavailability of Compound (I) Tosylate Form A

Figure 4:
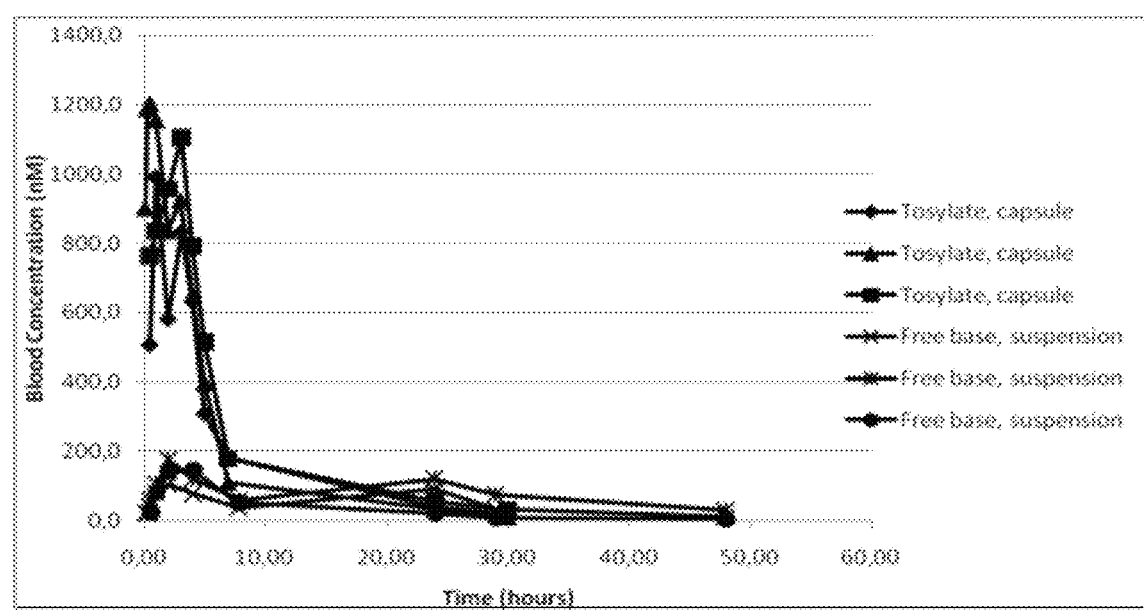
FIG. 4 shows the blood concentration (nM) in a dog after administration of compound (I) tosylate Form A (equivalent to 1.0 mg/kg compound (I) free base) in a gelatine capsule and the free base of compound (I) (0.8 mg/kg) administered in an aqueous suspension. The x-axis shows time (hours), the y-axis shows the blood concentration (nM) in the dog.

The difference in bioavailability for the compound (I) tosylate Form A in a gelatine capsule compared to crystalline compound (I) free base in an aqueous suspension was measured in the dog study described below:

Beagle dogs (three dogs for each formulation) were administered orally with Compound (I) tosylate form A (dose equivalent to 1.0 mg/kg compound (I) free base) in a gelatine capsule or an aqueous suspension of 0.8 mg/kg crystalline compound (I) free base suspended in water together with 1.2% w/w Avicel and 0.1% w/w Polysorbate 80. The measured plasma concentration of compound (I) following oral administration is shown in FIG. 4.

The bioavailability calculated from the results of the dog study was about 38% for compound (I) tosylate Form A in capsule and only about 12% for the free base in the aqueous suspension. Accordingly the bioavailability of compound (I) tosylate Form A was about 3 times higher than the free base.

Example 10

Tablet Formulation of Compound (I) Tosylate Form A Prepared by Roller Compaction A coated tablet formulation containing the components shown in Table 4 was prepared using the roller compaction and coating processes described below.

TABLE 4

| Materials | Quantity (mg per tablet) | Quantity per batch (kg) |
| --- | --- | --- |
| Compound (I) tosylate Form A (micronised)[1] (equivalent to 30 mg compound (I)) | 39.9 | 1.98 |
| Cellulose, microcrystalline (MCC) (Avicel PH101, SCG) | 314.1 | 15.72 |
| Dibasic calcium phosphate dihydrate (ex ThermoPhos) | 20.0 | 1.00 |
| Crosslinked polyvinylpyrrolidone (Kollidon CL, ex BASF) | 16.0 | 0.80 |
| Sodium lauryl sulfate (SDS) | 4.0 | 0.20 |
| Sodium stearyl fumarate | 6.0 | 0.30 |

[1]The 39.9 mg/tablet of compound (I) tosylate shown in Table 4 was equivalent to 39.5 mg/tablet of 100% pure compound (I) tosylate Form A.

Tablet Core

Compound (I) tosylate was delumped by milling through a suitable screen and was then mixed with about two thirds of the microcrystalline cellulose in a tumbling mixer. The premix was delumped by milling through a suitable screen. The dibasic calcium phosphate dihydrate, cross linked polyvinylpyrrolidone, SDS (milled) and remaining microcrystalline cellulose were then each delumped in a similar way. The premix and excipients were then mixed together in a tumbling mixer to produce a homogeneous mix. Two thirds of the sodium stearyl fumarate was screened and blended with the mix, which was then dry granulated in using a conventional roller compactor (Alexanderwerk WP 120×40V). The resultant granules were mixed with the remaining screened sodium stearyl fumarate and pressed into tablet cores. Eight batches pressed together to tablet cores.

Tablet Coating

The tablet cores (4 batches of 40 kg) were then coated using a conventional pan coater. The film coat was applied by spraying an aqueous suspension of the hydroxypropyl methylcellulose, PEG 6000 and titanium dioxide onto the tablet cores. The tablet coating consisted of hydroxypropyl methyl cellulose (Hydromellose 6 Pas) 10.6 mg, polyethylene glycol 6000 (PEG6000) 2.7 mg and titanium dioxide 2.7 mg per tablet.

Tablets containing compound (I) tosylate Form A providing the equivalent of 2.5 mg and 10 mg compound (I) were prepared using an analogous method by increasing the amount of microcrystalline cellulose to compensate for the lower quantity of compound (I) tosylate Form A present in the lower strength tablets. Therefore, the tablet cores had a constant weight (i.e. the sum of the quantities of the compound (I) tosylate Form A and microcrystalline cellulose was the same (approximately 354 mg/tablet) for the 2.5, 10 and 30 mg tablets).

Dissolution

Figure 5:
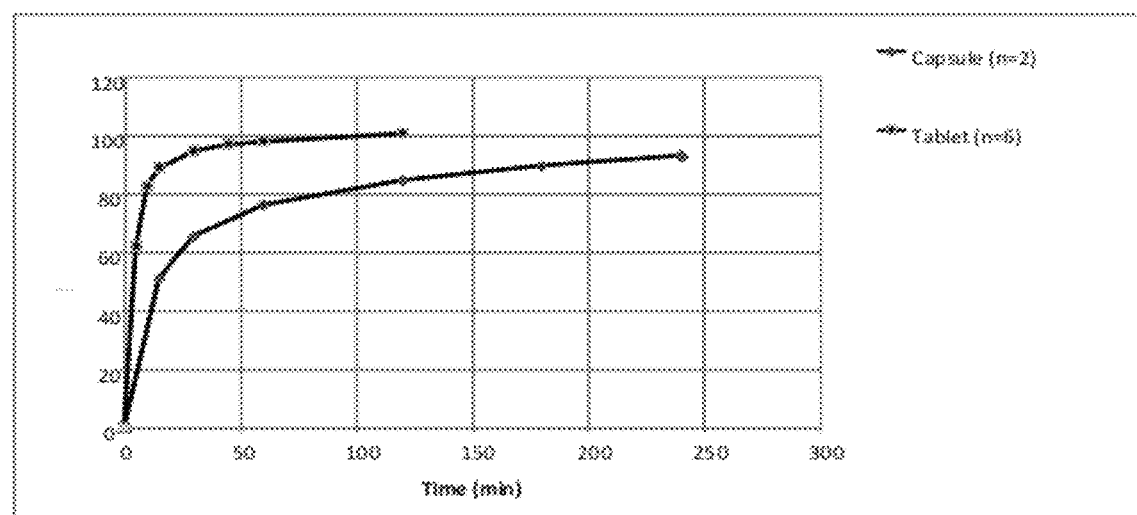
FIG. 5 shows the dissolution profiles of a film-coated tablet containing compound (I) tosylate Form A (equivalent to 30 mg compound (I) free base) described in Example 10 (square data points) and compound (I) tosylate Form A (equivalent to 30 mg compound (I) free base) in a capsule (diamond data points). The dissolution was measures in 900 ml of 0.1 M HCl (pH 1) as described in Example 10. The x-axis shows time (minutes), the y-axis shows % dissolved compound (I).

The dissolution profile of a tablet core prepared as described in Table 4 containing compound (I) tosylate Form A (equivalent to 30 mg compound (I) free base) was compared to the dissolution of crystalline compound (I) tosylate Form A (equivalent to 30 mg compound (I) free base) in a capsule. The dissolution was measured in 900 ml of 0.1 M HCl (pH 1) and using a USP dissolution apparatus 2 (paddle) at 75 rpm and 37° C. in a fully automated system, Zymark Multidose G3. Analysis was made by UV spectrophotometer with a detection wavelength of 337 nm. The results are shown in FIG. 5. The tablet prepared according to Table 4 (diamond data points) resulted in a higher dissolution rate of compound (I) tosylate Form A compared to dissolution of compound (I) tosylate Form A alone from a capsule (square data points).

Example 11

Tablet Formulation of Compound (I) Tosylate Form A Prepared by Direct Compression Tablets with the composition shown in Table 5 below were prepared as follows.

TABLE 5

| Materials | Quantity (mg per tablet) |
| --- | --- |
| Compound (I) tosylate Form A (micronised) | 39.5 |
| Cellulose, microcrystalline (MCC) (Avicel PH101, SCG) | 316.5 |
| Dibasic calcium phosphate dihydrate (ex ThermoPhos) | 20.0 |
| Crosslinked polyvinylpyrrolidone (Kollidon CL, ex BASF) | 16.0 |
| Sodium lauryl sulfate (SDS) | 4.0 |
| Sodium stearyl fumarate | 4.0 |

About one third of the microcrystalline cellulose (i.e. one third of total amount of 158.2 g=about 53 g) was sieved and mixed with sieved micronised compound (I) tosylate Form A (19.8 g). Dibasic calcium phosphate dihydrate (10 g), cross-linked polyvinylpyrrolidone (8.0 g) and SDS (ground in a mortar, 2.0 g) were each sieved and added to the mixture of the compound (I) tosylate Form A. The remaining microcrystalline cellulose was sieved and added to the powder mixture that was then mixed in a tumbling mixer. Sieved sodium stearyl fumarate (1.0 g) was added to 99 g of the mixed powder, which was pressed into tablets using commercially available equipment (i.e. Diaf™20).

Example 12

Tablet Formulation of Compound (I) Tosylate Form A Prepared by Roller Compaction A tablet formulation containing the components shown in Table 6 was prepared using the roller compaction process described below.

TABLE 6

| Materials | Quantity (mg per tablet) |
| --- | --- |
| Compound (I) tosylate Form A | 39.5 |
| Cellulose, microcrystalline (MCC) (Avicel PH101, SCG) | 314.5 |
| Dibasic calcium phosphate dihydrate (ex ThermoPhos) | 20.0 |
| Crosslinked polyvinylpyrrolidone (Kollidon CL, ex BASF) | 16.0 |
| Sodium lauryl sulfate (SDS) | 4.0 |
| Sodium stearyl fumarate | 6.0 |

About one third of the microcrystalline cellulose (i.e. one third of total amount 158 g=about 53 g) was sieved and mixed with sieved compound (I) tosylate Form A (20 g). Dibasic calcium phosphate dehydrate (10 g), cross-linked polyvinylpyrrolidone (8.0 g) and SDS (ground in a mortar, 2.0 g) were each sieved and added to the powder mixture containing the Compound (I) tosylate Form A. The remaining microcrystalline cellulose was sieved and added to the powder mixture that was then mixed in a tumbling mixer. Sieved sodium stearyl fumarate (1 g) was added to 95 g of the mixed powder and granulated using commercially to available roller compaction equipment (Vector TFC Labo). The granulated powder was mixed with sodium stearyl fumarate (0.4 g) and was pressed into tablets using commercially available equipment (i.e. Diaf™20)

Example 13

Effect of Dibasic Calcium Phosphate on Dissolution and Chemical Stability of Compound (I) Tosylate Form A Uncoated tablet cores containing the components shown in Table 7 were prepared using an analogous method to that described in Example 10, except that the mixture was dry granulated by slugging using a DIAF rather than roller compaction.

TABLE 7

| Materials | Quantity (% w/w) Formulation A | Quantity (% w/w) Formulation B |
| --- | --- | --- |
| Compound (I) tosylate Form A | 10 | 10 |
| Cellulose, microcrystalline (MCC) (Avicel PH101, SCG) | 78.5 | 83.5 |
| Dibasic calcium phosphate dihydrate (ex ThermoPhos) | 5 | — |
| Crosslinked polyvinylpyrrolidone (Kollidon CL, ex BASF) | 4 | 4 |
| Sodium lauryl sulfate (SDS) | 1 | 1 |
| Sodium stearyl fumarate | 1.5 | 1.5 |

The tablet cores were stored at 40° C. at 75% relative humidity for 4 weeks and then analysed for impurities compared to the tablets at the start of the test.

The impurities in the compositions were measured using a Waters Acquity HPLC with a Water HSS T3 C18-column (100×2.1 mm with 1.8 um particles), mobile phase a gradient with acetonitrile and 10 mM phosphate buffer pH 3.1, temperature 25° C. The amount of impurities was determined by the relative peak of the impurities. The results are shown in Table 8:

TABLE 8

| Formulation | Storage time (months) | Total amount of impurities (% w/w) |
| --- | --- | --- |
| A | 0 | <0.05 |
| A | 1 | 0.33 |
| B | 0 | <0.05 |
| B | 1 | 1.29 |

Dissolution

Figure 6:
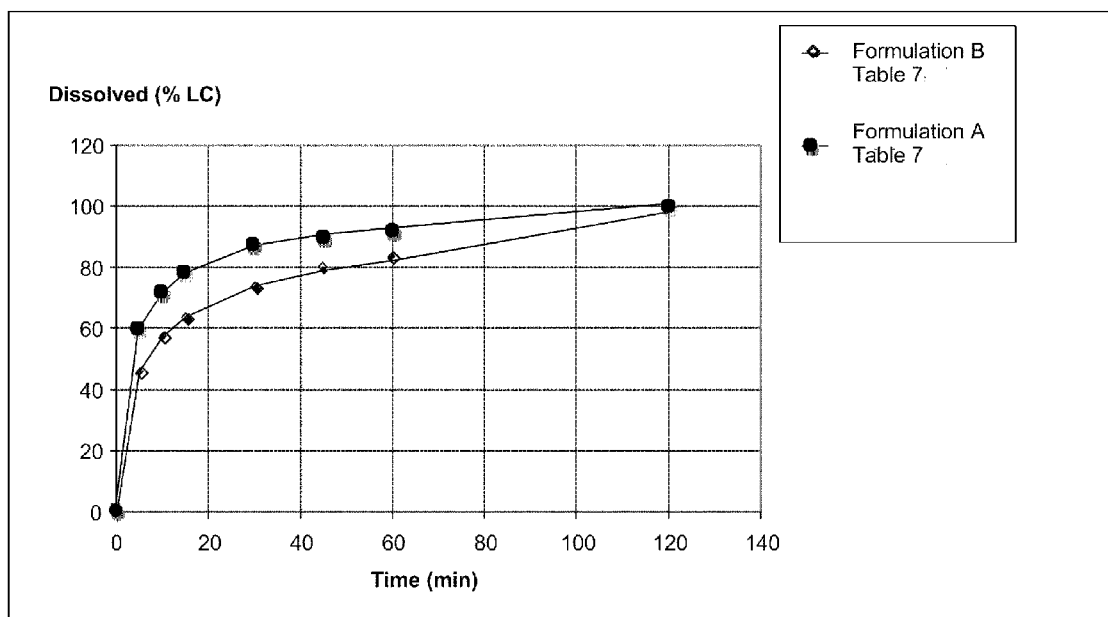
FIG. 6 shows the dissolution profile of tablet compositions A and B (active ingredient equivalent to 30 mg of compound (I) base) according to Table 7 (Example 13). Tablet formulation A containing 5% dibasic calcium phosphate is represented by square data points and tablet formulation B (0% dibasic calcium phosphate) is represented by diamond data points. The dissolution was measured in 900 ml of 0.1 M HCl (pH 1) as described in Example 13. The x-axis shows time (minutes), the y-axis shows % dissolved compound (I) (as % label claim (% LC)).

The dissolution profile of tablet formulations A and B in Table 7 were determined in 900 ml of 0.1 M HCl (pH 1) and using a USP dissolution apparatus 2 (paddle) at 75 rpm and 37° C. in a fully automated system, Zymark Multidose G3. Analysis was made by UV spectrophotometer with a detection wavelength of 337 nm. The results are shown in FIG. 6. This shows that the dissolution rate of Compound (I) tosylate was higher in formulation A containing the dibasic calcium phosphate than formulation B, which contained no dibasic calcium phosphate.

Example 14

Tablets Prepared by Roller Compaction

The tablet compositions shown in Table 9 were prepared using an analogous roller compaction method to that described in Example 12.

TABLE 9

| Materials | Quantity (% w/w) Formulation C | Quantity (% w/w) Formulation D |
| --- | --- | --- |
| Compound (I) tosylate Form A (micronised) | 10 | 10 |
| Cellulose, microcrystalline (MCC Avicel PH302) | 79 | — |
| Isomalt (Galen IQ) | — | 79 |
| Dibasic calcium phosphate dihydrate (ex. ThermoPhos) | 5 | 5 |
| Crosslinked polyvinylpyrrolidone (Kollidon CL, ex BASF) | 4 | 4 |
| Sodium lauryl sulfate (SDS) | 1 | 1 |
| Sodium stearyl fumarate | 1 | 1 |

Dissolution

The dissolution of tablet formulations C and D in Table 9 was measured using a USP dissolution apparatus 2 (paddle) at 75 rpm and 37° C. in a Zymark Multidose G3 system, 0.05 M phosphate buffer at pH 6.8 in a dissolution volume of 900 ml. Analysis was made by UV spectrophotometer with a detection wavelength of 337 nm. The results are shown in FIG. 3.

Example 15

Tablet Composition Containing Compound (I) Tosylate Form A, Lactose and Microcrystalline Cellulose The tablet composition shown in Table 10 was prepared by mixing the components, other than the lubricant using an analogous method to that described in Example 10, followed by slugging and milling of the mixture. The resulting powder was mixed with lubricant followed by tabletting.

TABLE 10

| Components | Quantity (per tablet) | Function |
| --- | --- | --- |
| Compound (I) tosylate Form A (corresponding to 30 mg Compound (I)) | 39.5 | Active substance |
| Cellulose, microcrystalline/ Microcrystalline cellulose | 20 | Diluent |
| Crospovidone | 16 | Disintegrant |
| Lactose monohydrate | 312.5 | Diluent |
| Sodium lauryl sulphate | 4 | Surfactant |
| Sodium stearyl fumarate | 8 | Lubricant |

Example 16

Preparation of Compound (I) Tosylate Form B

Example 16a

A solution of compound (I) tosylate Form A (5.9 mg) in THF (5 ml) was prepared at room temperature in a vial. Cyclohexane (1 ml) was added rapidly to the solution. The mixture was then allowed to evaporate to dryness at room temperature to afford compound (I) tosylate Form B.

Example 16b

A solution of compound (I) tosylate Form A (5 mg) in dioxane (5 ml) was prepared at room temperature in a vial. The vial was then covered with a pierced aluminium foil and the mixture allowed to stand at 5° C. until the solvents had evaporated to afford compound (I) tosylate Form B.

The X-ray powder diffraction of Compound (I) tosylate Form B is shown in FIG. 7.

Biological Activity
Human Neutrophil Elastase Quenched-Fret Assay

The assay uses Human Neutrophil Elastase (HNE) purified from serum (Calbiochem art. 324681; Ref. Baugh, R. J. et al., 1976, Biochemistry. 15, 836-841). HNE was stored in 50 mM sodium acetate (NaOAc), 500 mM sodium chloride (NaCl), pH 5.5 with added 50% glycerol at −20° C. The protease substrate used was Elastase Substrate V Fluorogenic, MeO-Suc-AAPV-AMC (Calbiochem art. 324740; Ref. Castillo, M. J. et al., 1979, Anal. Biochem. 99, 53-64). The substrate was stored in dimethyl sulfoxide (DMSO) at −20° C. The assay additions were as follows: Test compounds and controls were added to black 96-well flat-bottom plates (Greiner 655076), 1.0 µL in 100% DMSO, followed by 30 µL HNE in assay buffer with 0.01% Triton (trade mark) X-100 detergent. The assay buffer constitution was: 100 mM Tris(hydroxymethyl) aminomethane (TRIS) (pH 7.5) and 500 mM NaCl. The enzyme and the compounds were incubated at room temperature for 15 minutes. Then 30 µl substrate in assay buffer was added. The assay was incubated for 30 minutes at room temperature. The concentrations of HNE enzyme and substrate during the incubation were 1.7 nM and 100 µM, respectively. The assay was then stopped by adding 60 µl stop solution (140 mM acetic acid, 200 mM sodium monochloroacetate, 60 mM sodium acetate, pH 4.3). Fluorescence was measured on a Wallac 1420 Victor 2 instrument at settings: Excitation 380 nm, Emission 460 nm. $IC_{50}$ values were determined using Xlfit curve fitting using model 205.

When tested in the above assay, compound (I) (as the free base dissolved in DMSO) gave an $IC_{50}$ value for inhibition of human neutrophil elastase activity of 12 nM (n=26).

The invention claimed is:

1. The compound 6-methyl-5-(1-methyl-1H-pyrazol-5-yl)-N-{[5-methylsulfonyl)pyridin-2-yl]-methyl}-2-oxo-1-[3-trifluoromethyl)phenyl]-1,2-dihydropyridine-3-carboxamide 4-methylbenzenesulfonate Form A, wherein said Form A has an X-ray powder diffraction pattern measured using $CuK_\alpha$ radiation with at least one specific peak at 2θ=about 5.1, 7.3, 8.9, 17.0 or 17.8°.

2. The compound according to claim 1 wherein said Form A has an X-ray powder diffraction pattern measured using $CuK_\alpha$ radiation with specific peaks at 2θ=about 5.1, 7.3, 8.9, 17.0 and 17.8°.

3. The compound according to claim 1 wherein said Form A has an X-ray powder diffraction pattern measured using $CuK_\alpha$ radiation substantially the same as that shown in FIG. 1.

* * * * *